US009629720B2

(12) United States Patent
Nguyen et al.

(10) Patent No.: US 9,629,720 B2
(45) Date of Patent: Apr. 25, 2017

(54) APPARATUS AND METHODS FOR TREATING CARDIAC VALVE REGURGITATION

(71) Applicant: Jacques Seguin, Launen (CH)

(72) Inventors: Than Nguyen, Huntington Beach, CA (US); Jacques Seguin, Launen (CH)

(73) Assignee: Jacques Seguin, Launen (CH)

( * ) Notice: Subject to any disclaimer, the term of this patent is extended or adjusted under 35 U.S.C. 154(b) by 12 days.

(21) Appl. No.: 14/703,775

(22) Filed: May 4, 2015

(65) Prior Publication Data
US 2016/0324639 A1    Nov. 10, 2016

(51) Int. Cl.
A61F 2/24    (2006.01)

(52) U.S. Cl.
CPC .......... A61F 2/2454 (2013.01); A61F 2/246 (2013.01); A61F 2/2409 (2013.01); A61F 2/2427 (2013.01); A61F 2220/0016 (2013.01); A61F 2230/0095 (2013.01)

(58) Field of Classification Search
CPC ........ A61F 2/24; A61F 2/2409; A61F 2/2418; A61F 2/2412; A61F 2/2454; A61F 2/2463; A61F 2/2469
See application file for complete search history.

(56) References Cited

U.S. PATENT DOCUMENTS

| 4,490,859 | A | 1/1985 | Black et al. |
| 5,147,391 | A | 9/1992 | Lane |
| 5,213,575 | A | 5/1993 | Scotti |
| 5,376,114 | A | 12/1994 | Jarvik |
| 5,830,239 | A | 11/1998 | Toomes |
| 6,168,614 | B1 | 1/2001 | Andersen et al. |
| 6,269,819 | B1 | 8/2001 | Oz et al. |
| 6,461,382 | B1 | 10/2002 | Cao |
| 6,582,462 | B1 | 6/2003 | Andersen et al. |
| 6,613,086 | B1 | 9/2003 | Moe et al. |
| 6,911,043 | B2 | 6/2005 | Myers et al. |

(Continued)

FOREIGN PATENT DOCUMENTS

| WO | WO-2004/030568 A2 | 4/2004 |
| WO | WO-2010/106438 A2 | 9/2010 |
| WO | WO-2013/178335 A1 | 12/2013 |

OTHER PUBLICATIONS

International Search Report and Written Opinion dated Aug. 8, 2016 in Int'l PCT Patent Application Serial No. PCT/IB2016/052498.

Primary Examiner — David Isabella
Assistant Examiner — Leslie Lopez
(74) Attorney, Agent, or Firm — Foley & Lardner LLP; Christopher C. Bolten; Nicola A. Pisano

(57) ABSTRACT

Apparatus and methods for repairing a cardiac valve, e.g., a mitral valve, are provided. The apparatus may include an expandable frame defining a curved structure in the expanded deployed state and a membrane coupled to the expandable frame. The membrane may curve around a native leaflet, e.g., the posterior leaflet, in a first plane and curve around another leaflet, e.g., the anterior leaflet, in an orthogonal plane. The membrane may be adapted to be suspended in the flow path of the cardiac valve such a first surface of the membrane abuts the native leaflet during systole and a second surface of the membrane abuts the other native leaflet during systole, thereby reducing cardiac valve regurgitation.

15 Claims, 9 Drawing Sheets

(56) References Cited

U.S. PATENT DOCUMENTS

| | | |
|---|---|---|
| 7,037,333 B2 | 5/2006 | Myers et al. |
| 7,077,862 B2 | 7/2006 | Vidlund et al. |
| 7,399,315 B2 | 7/2008 | Iobbi |
| 7,562,660 B2 | 7/2009 | Saadat |
| 7,591,847 B2 | 9/2009 | Navia et al. |
| 7,691,144 B2 | 4/2010 | Chang et al. |
| 7,914,569 B2 | 3/2011 | Nguyen et al. |
| 8,002,825 B2 | 8/2011 | Letac et al. |
| 9,011,523 B2 | 4/2015 | Seguin |
| 2005/0010287 A1* | 1/2005 | Macoviak ............ A61F 2/2445 623/2.36 |
| 2005/0137690 A1 | 6/2005 | Salahieh et al. |
| 2005/0143689 A1 | 6/2005 | Ramsey, III |
| 2005/0228495 A1 | 10/2005 | Macoviak |
| 2005/0267573 A9 | 12/2005 | Macoviak et al. |
| 2006/0058871 A1 | 3/2006 | Zakay et al. |
| 2007/0265701 A1 | 11/2007 | Gurskis et al. |
| 2008/0033541 A1 | 2/2008 | Gelbart et al. |
| 2008/0065204 A1 | 3/2008 | Macoviak et al. |
| 2008/0125860 A1 | 5/2008 | Webler et al. |
| 2009/0069890 A1 | 3/2009 | Suri et al. |
| 2011/0022165 A1 | 1/2011 | Oba et al. |
| 2012/0215303 A1 | 8/2012 | Quadri et al. |
| 2012/0271398 A1 | 10/2012 | Essinger et al. |
| 2013/0023985 A1* | 1/2013 | Khairkhahan ........ A61F 2/2466 623/2.38 |
| 2015/0119981 A1 | 4/2015 | Khairkhahan et al. |

\* cited by examiner

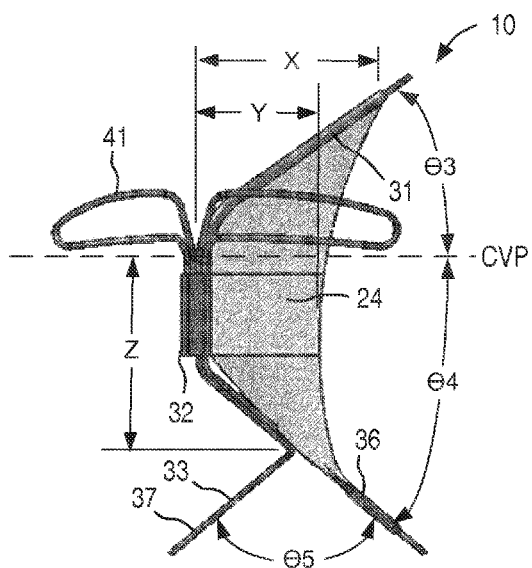
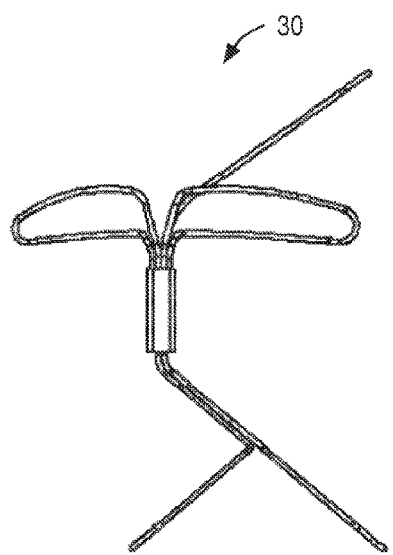
FIG. 9A   FIG. 9B
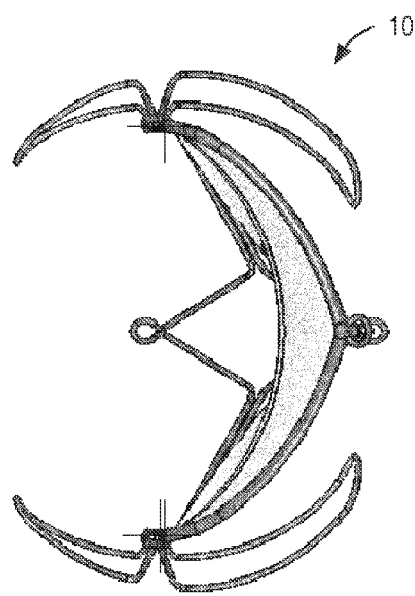
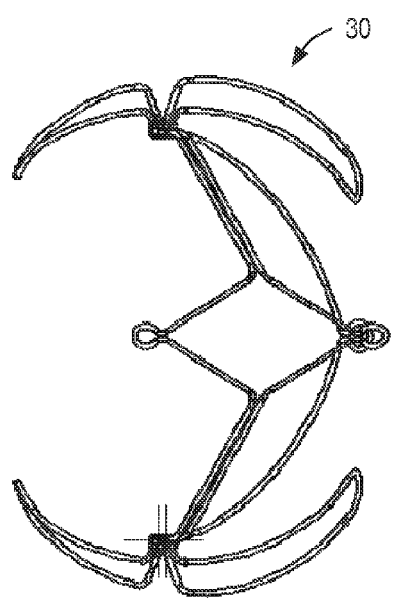
FIG. 10A   FIG. 10B

APPARATUS AND METHODS FOR TREATING CARDIAC VALVE REGURGITATION

I. FIELD OF THE INVENTION

This application generally relates to apparatus and methods for performing transcatheter or minimally invasive repair of a defective cardiac valve, such as the mitral, tricuspid, pulmonary, and aortic valves.

II. BACKGROUND OF THE INVENTION

The human heart has four major valves which moderate and direct blood flow in the cardiovascular system. These valves serve critical functions in assuring a unidirectional flow of an adequate blood supply through the cardiovascular system. The mitral valve and aortic valve control the flow of oxygen-rich blood from the lungs to the body. The mitral valve lies between the left atrium and left ventricle, while the aortic valve is situated between the left ventricle and the aorta. Together, the mitral and aortic valves ensure that oxygen-rich blood received from the lungs is ejected into systemic circulation. The tricuspid and pulmonary valves control the flow of oxygen-depleted blood from the body to the lungs. The tricuspid valve lies between the right atrium and right ventricle, while the pulmonary valve is situated between the right ventricle and the pulmonary artery. Together the tricuspid and pulmonary valves ensure unidirectional flow of oxygen-depleted blood received from the right atrium towards the lungs.

Heart valves are passive structures composed of leaflets that open and close in response to differential pressures on either side of the valve. The mitral valve acts as the inflow valve to the left side of the heart. Blood flows from the lungs, where it absorbs oxygen, and into the left atrium. When the mitral valve opens, blood flows from the left atrium to the left ventricle. The mitral valve then closes to prevent blood from leaking back into the lungs when the ventricle contracts to pump blood out to the body. Whereas the aortic, pulmonary, and tricuspid valves have three leaflets, the mitral valve has only two leaflets.

These heart valves may be rendered less effective by acute or chronic ischemic disease of the heart, congenital, inflammatory, or infectious conditions, or disease, all of which may lead to dysfunction of the valves over time. Such degradation may result in serious cardiovascular compromise or even death. Because the left ventricle drives systemic circulation, it generates higher pressures than the right ventricle, and accordingly the aortic and mitral valves are more susceptible to dysfunction, such as stenosis or regurgitation. A stenotic mitral valve may impede blood flow into the heart, causing blood to back up and pressure to build in the lungs. Consequently, the presence of a stenotic valve may make it difficult for the heart to increase the amount of blood pumped during exercise, producing shortness of breath under physical activity. Regurgitation occurs when the mitral valve leaflets do not coapt correctly, thus causing blood to leak backwards into the left atrium and lungs each time the heart pumps. Improper coaptation of the mitral valve leaflets thus requires the heart to pump more blood with each contraction to eject the necessary amount of blood for systemic circulation; a process called volume overload. Although the heart may compensate for this overload for months to years, provided the progression of the leakage comes gradually, the heart will eventually begin to fail, producing shortness of breath and fatigue. Mitral valve dysfunction is rarely caused by congenital conditions, but is largely the result of degenerative disease due to advancing age, disease, or infection.

Loose chordae tendineae may result, for example, from ischemic heart disease affecting the papillary muscles. The papillary muscles attach to the chordae tendineae and keep the leaflets of a valve shut. Some forms of ischemic cardiac disease cause the papillary muscles to lose their muscle tone, resulting in a loosening of the chordae tendineae. This loosening, in turn, allows the leaflets of the affected valve to prolapse, causing regurgitation.

FIG. 1 illustrates the anatomy of a mitral valve MV having an anterior leaflet AL and a posterior leaflet PL. The mitral valve MV illustrated in FIG. 1 is defective as the mitral valve leaflets (AL and PL) do not coapt correctly, leaving one or more gaps between the leaflets, resulting in regurgitation. The valve leaflets AL, PL are tethered to the endocardium of the left ventricle via the chordae tendineae CT and the antero-lateral papillary muscle ALPM and the postero-medial papillary muscle PMPM. The valve leaflets AL, PL connect at the antero-lateral commissure ALC and the posterior-medial commissure PMC. The annulus circumscribes the valve leaflets AL and PL and the portion of the annulus adjacent the anterior leaflet AL may be referred to as the anterior annulus AA while the portion of the annulus adjacent the posterior leaflet PL may be referred to as the posterior annulus PA.

FIG. 2A illustrates the anatomy of a mitral valve MV looking down from the left atrium. The mitral valve MV illustrated in FIG. 2A is considered healthy as the mitral valve leaflets (AL and PL) coapt correctly, leaving no gaps between the leaflets. Three segments in the anterior leaflet AL are often referred to as A1, A2, and A3 while corresponding segments in the posterior leaflet PL are referred to as P1, P2, and P3. FIG. 2B illustrates the mitral valve MV with representative planes shown solely for reference, including cardiac valve plane CVP, first flowpath plane FP1, and second flowpath plane FP2. Cardiac valve plane CVP, first flowpath plane FP1, and second flowpath plane FP2 are preferably orthogonal to one another and may be analogous to x, y, and z planes as commonly used in mathematics. Cardiac valve plane CVP is substantially parallel to, and runs through, the cardiac valve and its leaflets in the closed state. First flowpath plane FP1 runs through the general region where the crest of a cardiac leaflet, e.g., anterior leaflet AL, meets another cardiac leaflet, e.g., posterior leaflet PL, or where, in a defective valve, the crest should meet the other leaflet. Second flowpath plane FP2 intersects first flowpath plane FP1 generally at the crest of the cardiac valve and generally runs through the center of the opening formed when the cardiac leaflets are in the open state. Illustratively, the planes are shown on a mitral valve, although it should be understood that these planes may be used for reference with other cardiac valves such as the tricuspid valve TV, aortic valve AV, or pulmonary valve PV.

Previously known medical treatments to address diseased valves generally involve either repairing the diseased native valve or replacement of the native valve with a mechanical or biological valve prosthesis. Previously-known valve prostheses have some disadvantages, such as need for long-term maintenance with blood thinners, the risk of clot formation, limited durability, etc. Accordingly, valve repair, when possible, usually is preferable to valve replacement. However, most dysfunctional valves are too diseased to be repaired using previously known methods and apparatus. Accordingly, a need exists for a prosthesis capable of assisting heart valve function that enables treatment of a larger patient population, while reducing the need to fully supplant the native heart valve.

For many years, the standard treatment for such valve dysfunction called for surgical repair or replacement of the valve during open-heart surgery, a procedure conducted under general anesthesia. An incision is made through the patient's sternum (sternotomy), and the heart is accessed and stopped while blood flow is rerouted through a heart-lung bypass machine. When replacing the valve, the native valve is excised and replaced with either a mechanical or biological prosthesis. However, these surgeries are prone to many complications and long hospital stays for recuperation.

More recently, transvascular techniques have been developed for introducing and implanting a replacement valve, using a flexible catheter in a manner less invasive than open-heart surgery. In such techniques, a replacement valve is mounted in a crimped state at the end of a flexible catheter, and then advanced through the blood vessel of a patient until the prosthetic valve reaches the implantation site. The valve then is expanded to its functional size at the site of the defective native valve, usually by inflating a balloon within where the valve has been mounted. By expanding the prosthetic valve, the native valve leaflets are generally pushed aside and rendered ineffective. Examples of such devices and techniques, wherein the native valve is replaced in its entirety by a substitute tissue valve, are described, for example, in U.S. Pat. Nos. 6,582,462 and 6,168,614 to Andersen et al.

Mitral valve repair has become increasingly popular due to its high rates of success and the clinical improvements noted after repair. Several technologies have been developed to make mitral repair less invasive. These technologies range from iterations of the Alfieri stitch procedure; to coronary sinus-based modifications of mitral anatomy; to subvalvular placations or ventricular remodeling devices, which also may be employed to correct mitral valve regurgitation. Unfortunately, for a significant percentage of patients, mitral valve replacement is still necessary due to stenosis or anatomical limitations, and few less-invasive options are available for replacement procedures.

Prostheses have been produced and used for over forty years to treat cardiac disorders. They have been made from a variety of materials, both biological and artificial. Mechanical or artificial valves generally are made from non-biological materials, such as plastics or metals. Such materials, while durable, are prone to blood clotting and thrombus formation, which in turn increases the risk of embolization and stroke or ischemia. Anticoagulants may be taken to prevent blood clotting that may result in thromboembolic complications and catastrophic heart failure, however, such anti-clotting medication may complicate a patient's health due to the increased risk of hemorrhage.

In contrast, "bio-prosthetic" valves are constructed with leaflets made of natural tissue, such as bovine, equine or porcine pericardial tissue, which functions very similarly to the leaflets of the natural human heart valve by imitating the natural action of the heart valve leaflets, coapting between adjacent tissue junctions known as commissures. The main advantage of valves made from tissue is they are not as prone to blood clots and do not absolutely require lifelong systemic anticoagulation. A major disadvantage of tissue valves is they lack the long-term durability of mechanical valves. This is so because naturally occurring processes within the human body may stiffen or calcify the tissue leaflets over time, particularly at high-stress areas of the valve such as at the commissure junctions between tissue valve leaflets and at the peripheral leaflet attachment points, or "cusps," at the outer edge of each leaflet. Furthermore, valves are subject to stresses from constant mechanical operation within the body. In particular, the leaflets are in tension when in a closed position and are in compression when in an open position. Such tension causes prosthetic valves to wear out over time, requiring replacement.

In recent years, bio-prosthetic valves have been constructed by integrating valve leaflets made from natural tissue into the stent-like supporting frame, which provides a dimensionally stable support structure for the valve leaflets. In more advanced prosthetic heart valve designs, besides providing dimensionally stable support structure for the valve leaflets, the stent-like supporting frame also imparts a certain degree of controlled flexibility, thereby reducing stress on the leaflet tissue during valve opening and closure and extending the lifetime of the leaflets. In most designs, the stent-like supporting frame is covered with a biocompatible cloth (usually a polyester material such as Dacron™ or polytetrafluoroethylene (PTFE)) that provides sewing attachment points for the leaflet commissures and leaflets themselves. Alternatively, a cloth-covered suture ring may be attached to the stent-like supporting frame, providing a site for sewing the valve structure in position within the patient's heart during a surgical valve replacement procedure.

While iterative improvements have been made on surgical bioprosthetic valves over the last several decades, existing bioprosthetic valves still have drawbacks. One drawback is the mismatch in size and mass between opposing surfaces of the stent-like supporting frame. The mismatch is often due to the variability in the shapes and mechanical characteristics of the stent-like supporting frame. For prosthetic valves with balloon-expandable stent-like supporting frames, the recoil of the supporting frames post-balloon-inflation may lead to perivalvular leaks around the circumference of the prosthetic valve and potential slippage and migration of the valve post-implantation. Another risk associated with prosthetic valves having balloon-expandable supporting frames is potential damage to the leaflets of the prosthesis during implantation, when the leaflets may be compressed between the balloon and the supporting frame. For prosthetic valves with self-expanding stent-like supporting frames, mismatch may arise due to the deformation/movement of the supporting frame, e.g., slight deformation of the frame into a less than circular shape during normal cardiac movement. Such mismatch may lead to instability among components of a prosthetic valve, resulting in perivalvular leaks and uneven stress distribution in the valve leaflets, resulting in accelerated wear of the valve.

Another drawback in the construction of existing bio-prosthetic valves with self-expanding supporting frames is the potential for damage to the leaflet tissue arising from the spacing between the struts of the frame. For example, when the stent-like supporting frame is deployed, the distance between struts during expansion of the frame may stretch both the surrounding tissue and the leaflet tissue further apart than designed, potentially resulting in damage to surrounding tissue and leaflet tissue. With use of an oblong or circular radially self-expanding frame applied on the majority of the mitral valve, there is risk of left-ventricular outflow tract (LVOT) obstruction.

A mitral valve regurgitation often arises due to mitral annulus dilatation, which may be treated using a surgical technique to narrow and restore the natural shape the annulus. Usually the mitral valve and annulus are shaped like a "D", but when dilated the shape becomes more like an "O".

Prosthetic annuloplasty rings are therefore an important additional component in some mitral valve repair techniques. A primary role of the annuloplasty ring is to reduce the size of the annulus and decrease the tension on the sutures while providing flexibility and mobility at the same time. An annuloplasty ring thus is omitted during mitral valve repair only in cases of infective endocarditis, in order to avoid excess foreign material. When an annuloplasty ring is used, three months of anticoagulation is often prescribed.

One recent technique for correcting mitral valve leakage, as described for example in U.S. Pat. No. 6,269,819 to Oz et al., employs a percutaneously placed catheter to introduce a clipping apparatus into a leaking mitral valve. Once positioned, the clip arms are unfolded and advanced into the left ventricle below the valve leaflets, after which it is retracted and closed over the leaflets, holding them together to reduce mitral regurgitation. If further improvements to regurgitation are to be made, the clip is released and further advanced for repositioning. Once decrease of leakage has been assessed, the clip is deployed to entrap together the free edges of the mitral leaflets, and the catheter withdrawn. The clip may be made of metal with a polyester fabric covering to promote healing. Because the clip transforms the mitral orifice into two orifices, the clip may significantly obstruct the flow of blood through the valve.

Mitral regurgitation is generally due to ischemic dilatation of the left ventricle creating an annular dilatation, chordal, and papillary muscle downward displacement and left ventricle distension that may be treated by a surgical or a percutaneous mitral valve replacement using, for example, a device constructed in accordance with U.S. Patent Pub. No. 2012/0215303 to Quadri, the entire contents of which are incorporated herein by reference. These techniques have the drawback of replacing a mitral valve that is itself generally normal or subnormal. The mitral valve has an important role in the left ventricle function. Ideally, the mitral valve should be repaired rather than replaced in such patients with an already diseased low ejection fraction left ventricle.

In view of the above-noted drawbacks of previously-known systems, it would be desirable to provide a device, and methods of using the same, that assists the functioning of the native cardiac valve, rather than removing or entirely supplanting the native valve. The native structures (mitral leaflets, chordae, papillary muscles, etc.) play an important role in left-ventricular function and therefore any valve replacement system that does not respect these elements may adversely impact the left-ventricular function.

III. SUMMARY OF THE INVENTION

The present disclosure overcomes the drawbacks of previously-known systems by providing apparatus and methods for repairing a cardiac valve, e.g., a mitral valve, a tricuspid valve, an aortic valve, or a pulmonary valve. The apparatus may include an expandable frame defining a curved structure in the expanded deployed state and a membrane coupled to the expandable frame. The membrane may curve around a native leaflet, e.g., the posterior leaflet, in a first plane and curve around another leaflet, e.g., the anterior leaflet, in an orthogonal plane. The membrane may be adapted to be suspended in the flow path of the cardiac valve such a first surface of the membrane abuts the native leaflet during systole and a second surface of the membrane abuts the other native leaflet during systole, thereby reducing cardiac valve regurgitation.

In accordance with one aspect of the present disclosure, a prosthetic device for repairing a cardiac valve defining a flow path bounded by a first native leaflet and a second native leaflet is provided. The cardiac valve may be a mitral valve or may be a tricuspid valve, an aortic valve, or a pulmonary valve bounded by a third native leaflet. The prosthetic device may include an expandable frame and a membrane coupled to the expandable frame. The expandable frame may be configured to transition from a contracted delivery state to an expanded deployed state. The expandable frame may define a curved structure in the expanded deployed state, whereby the curved structure is adapted to curve around the first native leaflet, e.g., posterior leaflet. The expandable frame may have one or more attachment portions adapted for securing the prosthetic device to cardiac tissue in the expanded deployed state. The membrane may be adapted to be suspended in the flow path and have a first surface and a second surface. The first surface may be adapted to abut the first native leaflet, e.g., posterior leaflet, during systole and the second surface may have a concave shape in a plane of the cardiac valve adapted to abut the second native leaflet, e.g., anterior leaflet, during systole, thereby reducing cardiac valve regurgitation.

The expandable frame may have an upper portion adapted to extend into a first heart chamber, e.g., left atrium, and a lower portion adapted to extend into a second heart chamber, e.g., left ventricle. Some or all of the upper portion may be adapted to curve toward a native annulus of the first native leaflet. The upper portion may form an upper lip adapted to hang over the first native leaflet or the native annulus or both. The upper portion may be adapted to be deployed in the first heart chamber and to not contact cardiac tissue when deployed. The membrane may be coupled to the expandable frame along the entire upper portion. Some or all of the lower portion may be adapted to curve toward a native annulus of the first native leaflet. The lower portion may have a compound angle to define a first section of the lower portion adapted to curve toward a first native annulus of the first native leaflet and a second section of the lower portion adapted to curve toward a second native annulus of the second native leaflet.

The membrane may be coupled to the expandable frame along at least some of the first section, but may not be coupled to the expandable frame along at least some of the second section. The membrane may not be coupled to the expandable frame to define at least one exposed portion of the lower portion, the exposed portion sized to reduce or eliminate contact between the lower portion and native chordae tendineae and to permit blood flow through the exposed portion. The first section may form a first section peak and the second section may form a second section peak. The first and second sections may be adapted to be deployed in the left ventricle and to not contact cardiac tissue when deployed.

A convex portion of the first surface at the plane of the cardiac valve may be sized and shaped to mimic the curve of the first native leaflet. The concave portion of the second surface at the plane of the cardiac valve may be sized and shaped to mimic the curve of the second native leaflet. The concave portion of the curved structure in a different plane may curve around the first native leaflet for 4 to 17 mm. The expandable frame having the membrane coupled thereto may be configured to be contracted within a delivery catheter during the contracted delivery state.

The one or more attachment portions may comprise a first banana-shaped portion adapted to be coupled to a cardiac valve annulus and a second banana-shaped portion adapted to be coupled to an opposing portion of the cardiac valve annulus. The one or more attachment portions may be adapted to be secured to cardiac tissue via one or more fixation devices configured to perforate a cardiac valve annulus.

The expandable frame may be configured to accommodate deployment of a replacement valve, such that the expandable frame serves as an anchor for the replacement valve. The expandable frame may include one or more strain relief members configured to permit deflection of the expandable frame to reduce strain during compression of the heart.

The prosthetic device may be adapted for deployment at the mitral valve and the concave portion of the curved structure may curves around a native posterior leaflet, the first surface may be adapted to abut the native posterior leaflet during systole, and the second surface may have the concave shape in the plane of the cardiac valve adapted to abut a native anterior leaflet during systole. The curved structure in the expanded deployed state may define a saddle-shaped structure.

IV. BRIEF DESCRIPTION OF THE DRAWINGS

FIGS. 9A and 9B are, respectively, side views of the exemplary prosthetic device and the exemplary expandable frame.

FIGS. 10A and 10B are, respectively, top views of the exemplary prosthetic device and the exemplary expandable frame.

Figure 14A:
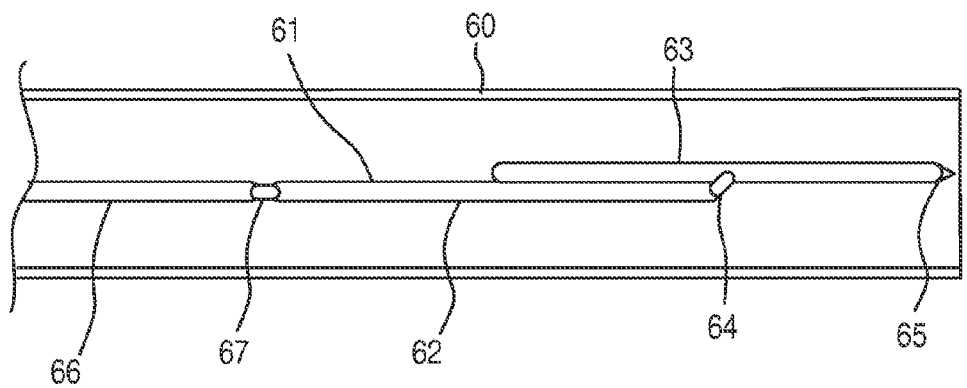
Figure 14B:
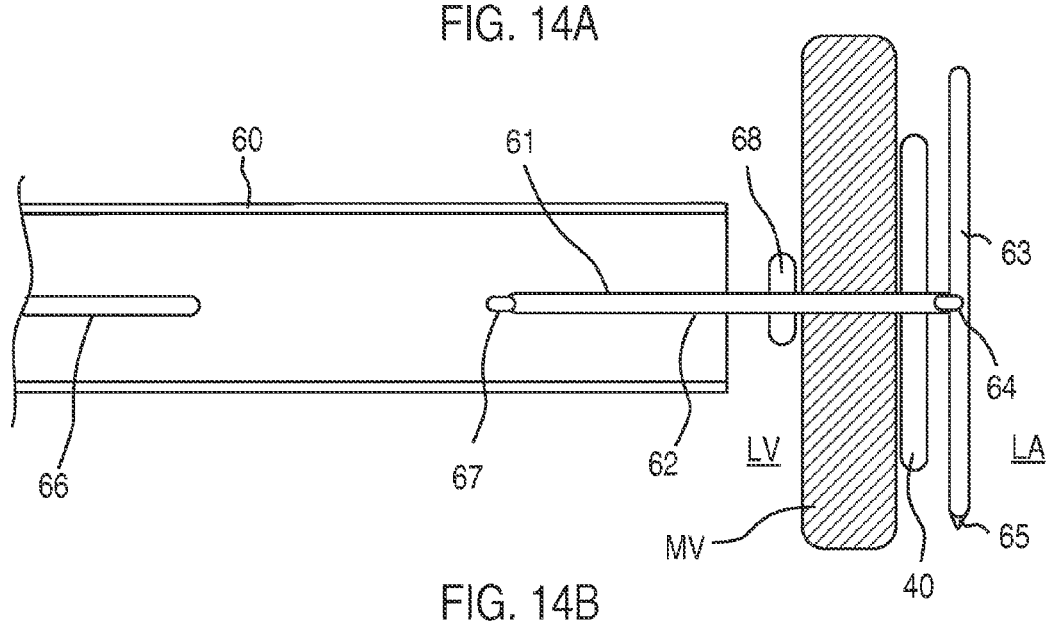
Figure 15:
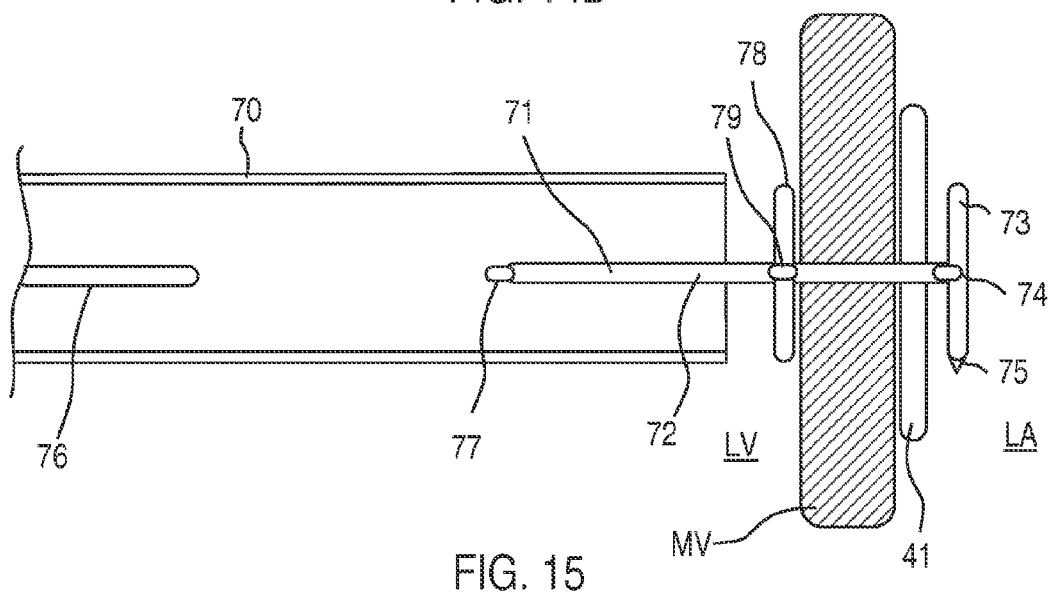

FIGS. 14A, 14B, and 15 depict illustrative embodiments of fixation catheters for transvascular delivery of fixation devices for fixing the prosthetic device to the mitral valve.

Figure 16A:
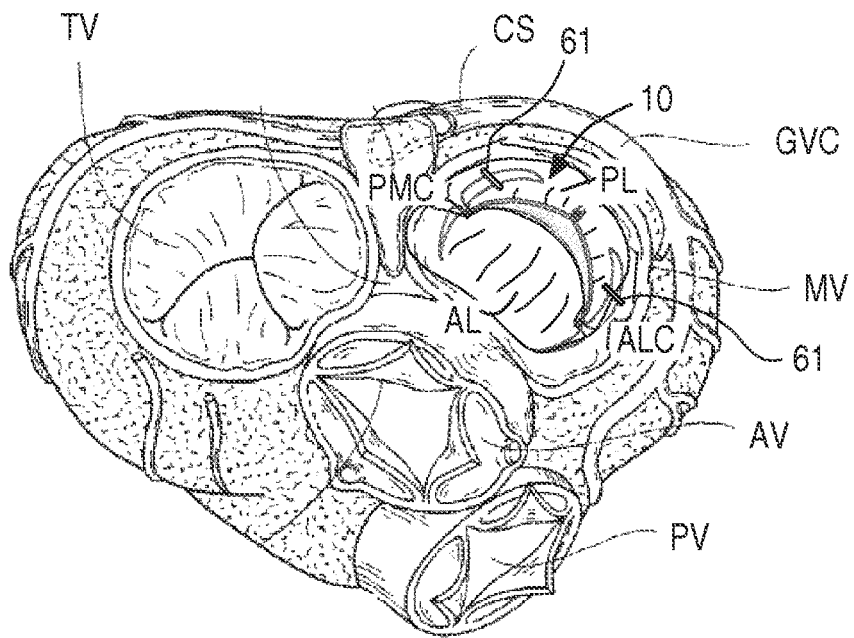
Figure 16B:
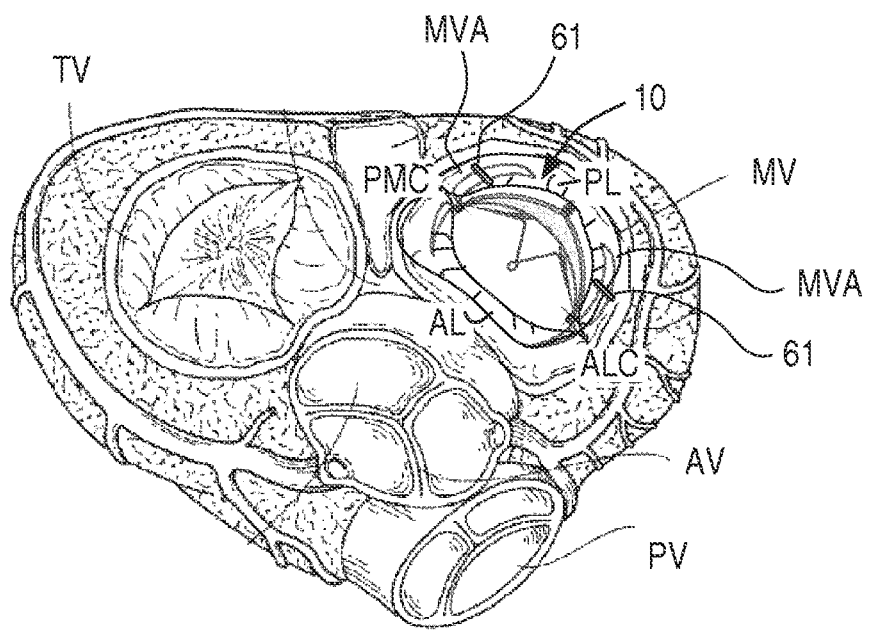

FIGS. 16A and 16B depict a heart in systole and diastole, respectively, having an exemplary prosthetic device of the present disclosure implanted in the mitral valve.

Figure 17A:
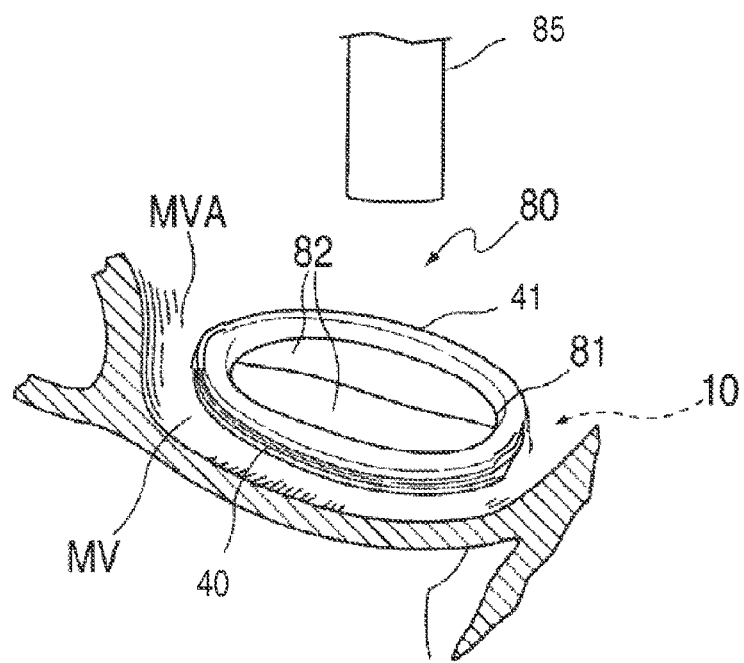

FIG. 17A is an illustrative view showing deployment of a replacement valve prosthesis at the site of a deployed prosthetic device of the present disclosure.

Figure 17B:
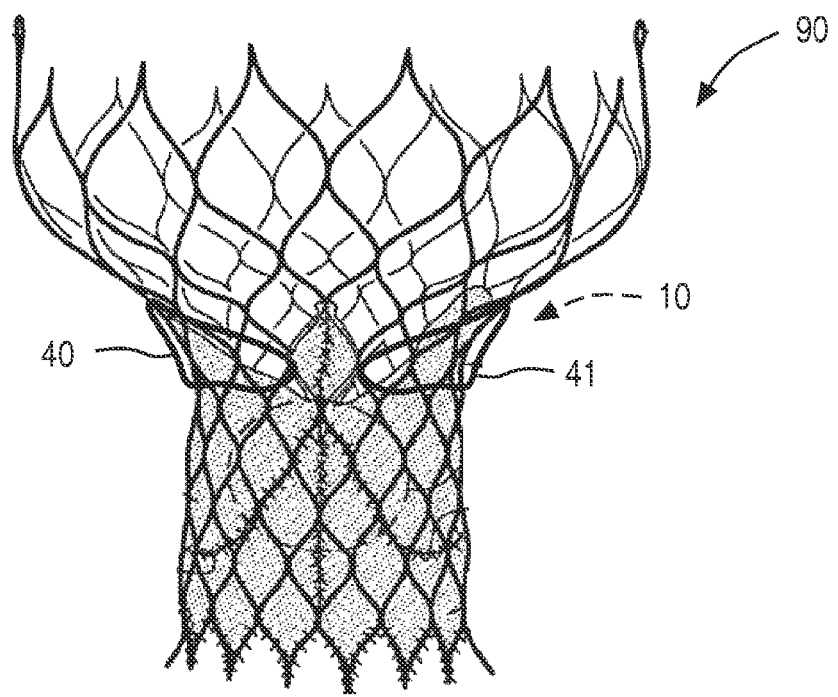

FIG. 17B is an illustrative view showing deployment of a self-expanding percutaneous replacement valve prosthesis at the site of a deployed prosthetic device of the present disclosure.

V. DETAILED DESCRIPTION OF THE INVENTION

Apparatus and methods of the present disclosure are designed for repairing a defective cardiac valve, such as a mitral valve, a tricuspid valve, a pulmonary valve, or an aortic valve. In accordance with the principles of the present disclosure, the apparatus and methods may be optimized for use in treating cardiac valve regurgitation when the leaflets of the cardiac valve do not coapt correctly, thus causing blood to leak backwards through the valve as the heart pumps. Advantageously, apparatus of the present disclosure are configured for implantation at a cardiac valve within a blood flowpath such that the native leaflets abut the apparatus during the portion of the cardiac cycle when the cardiac valve attempts to close, thereby enhancing native leaflet coaptation and minimizing regurgitation.

Figures 3A, 3B:
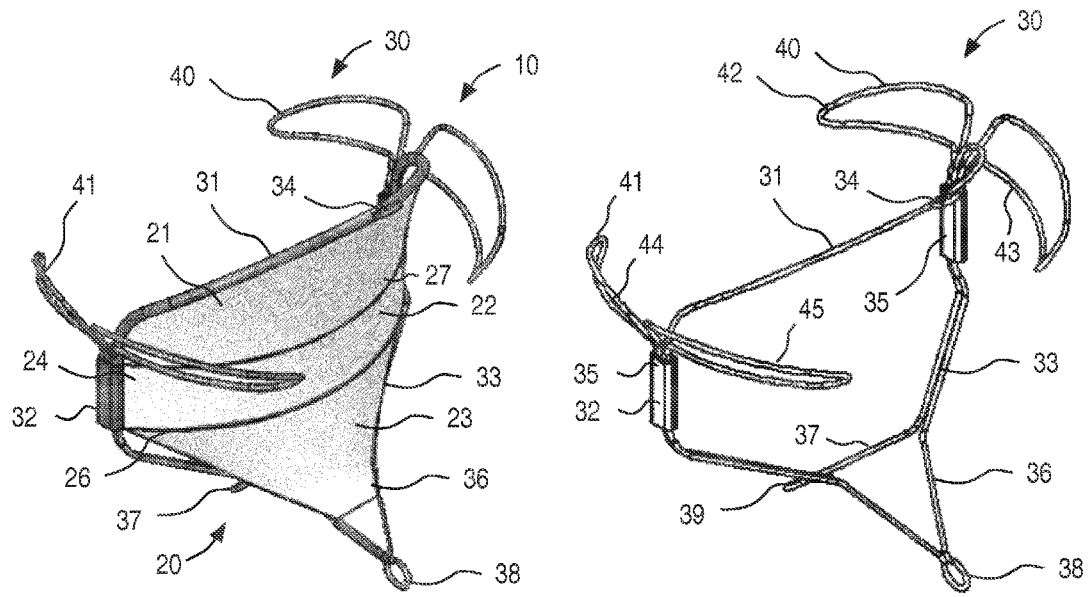
FIG. 3A depicts an exemplary embodiment of a prosthetic device constructed in accordance with the principles of the present disclosure in a perspective view.
FIG. 3B illustrates a perspective view of an exemplary expandable frame of the prosthetic device constructed in accordance with the principles of the present disclosure.

Referring to FIG. 3A, an illustrative embodiment of a prosthetic device in accordance with the principles of the present disclosure is described. Illustratively, the prosthetic device is designed for repairing a defective mitral valve, although it could be readily adapted for other cardiac valves such as the tricuspid valve, aortic valve, or pulmonary valve. In FIG. 3A, the upper portion of prosthetic device 10 may be adapted to extend into a patient's heart lumen or chamber, e.g., left atrium, while the lower portion of prosthetic device 10 may be adapted to extend into another heart lumen or chamber, e.g., left ventricle. Preferably, prosthetic device 10 is adapted for repairing a cardiac valve defining a flow path bounded by a native leaflet, e.g., posterior leaflet, and another native leaflet, e.g., anterior leaflet. Prosthetic device 10 includes membrane 20 mounted on expandable frame 30. As further described below, prosthetic device 10 preferably is configured to transition between an expanded deployed state and a contracted delivery state, such that the device may be disposed within a delivery catheter for transvascular or minimally-invasive surgical delivery.

Membrane 20 may be coupled to expandable frame 30 using sutures or biocompatible adhesive at a suitable location, e.g., between first and second attachment portions 40 and 41, and is preferably adapted to be suspended in the flow path of the cardiac valve. Membrane 20 may be a prosthetic leaflet as described in U.S. Pat. No. 9,011,523 to Seguin, the entire contents of each are incorporated herein by reference, and membrane 20 may be a single layer or multi-layered. Membrane 20 has a thickness; e.g., between about 0.1 mm to 10 mm, between about 0.1 mm to 5 mm, between about 0.1 mm to 1 mm, between about 0.1 mm to 0.5 mm; that may be relatively uniform or may vary throughout portions of the membrane. Membrane 20 illustratively includes upper portion 21, intermediate portion 22, and lower portion 23. Membrane 20 may also include first surface 24 adapted to face a native leaflet, e.g., posterior leaflet, and second surface 25 (shown in FIG. 4) adapted to face another native leaflet, e.g., anterior leaflet. In the illustrated embodiment, first and second surfaces 24 and 25 are on opposing sides of membrane 20.

Upper portion 21 of membrane 20 may be adapted to extend into a heart lumen or chamber, e.g., left atrium, and may not contact cardiac tissue when deployed, e.g., not contact the cardiac valve, not contact cardiac valve leaflets, not contact cardiac valve annulus, not contact cardiac vessel walls and/or not contact cardiac chamber walls. Some or all of upper portion 21 may curve toward cardiac tissue when deployed. For example, upper portion 21 may curve around a native leaflet, e.g., posterior leaflet, and toward a native annulus of the native leaflet, e.g., posterior annulus. In one embodiment, upper portion 21 is defined by a loop of expandable frame 30 which forms an upper lip adapted to hang over native cardiac tissue, e.g., posterior leaflet and/or posterior annulus, and preferably not contact such cardiac tissue.

Intermediate portion 22 of membrane 20 is adapted to be deployed at the cardiac valve in between the native cardiac leaflets. Preferably, at least at some of intermediate portion 22 is positioned in the cardiac valve plane CVP. In one embodiment, the apex of first surface 24 at intermediate portion 22 is adapted to be implanted approximately where cardiac valve plane CVP, first flowpath FP1, and second flowpath FP2 intersect. Intermediate portion 22 may have a curved structure in the cardiac valve plane CVP. For example, first surface 24 at intermediate portion 22 may have a convex shape and second surface 25 at intermediate portion 22 may have a concave shape. Intermediate portion 22 may, for example, have a C-shape and/or a crescent-shape in the cardiac valve plane CVP. In one embodiment, first surface 24 at intermediate portion 22 is sized and shaped to mimic the curve of a native leaflet, e.g., posterior leaflet, while second surface 25 at intermediate portion 22 is sized and shape to mimic the curve of another native leaflet, e.g., anterior leaflet. Such curvature around the posterior leaflet may be particularly advantageous in a patient having a defective cardiac valve due to expansion of the left side of the heart. Such expansion causes the posterior leaflet to be pulled away from the anterior leaflet, resulting in cardiac valve regurgitation. Cardiac disease, defects, and injury, such as ischemic cardiomyopathy, may cause left heart expansion.

First surface 24 is adapted to abut, preferably at least at intermediate portion 22, a native leaflet during a portion of the cardiac cycle. For example, first surface 24 may be adapted to abut the native posterior leaflet when the native posterior leaflet attempts to close during systole. Second surface 25 is adapted to abut, preferably at least at intermediate portion 22, another native leaflet during the portion of the cardiac cycle. For example, second surface 25 may be adapted to abut the native anterior leaflet when the native anterior attempts to close during systole. Such abutment is expected to enhance native leaflet coaptation and reduce cardiac valve regurgitation.

Lower portion 23 of membrane 20 may be adapted to extend into another heart lumen or chamber, e.g., left ventricle, and may not contact cardiac tissue when deployed, e.g., not contact the cardiac valve, not contact cardiac valve leaflets, not contact cardiac valve annulus, not contact cardiac vessel walls, not contact chordae tendineae, and/or not contact cardiac chamber walls. Some or all of lower portion 23 may curve toward cardiac tissue when deployed. For example, lower portion 23 may curve around a native leaflet, e.g., posterior leaflet, and toward a native annulus of the native leaflet, e.g., posterior annulus. In one embodiment, lower portion 23 is defined by a triangular portion of expandable frame 30 which forms an lower peak adapted to hang over native cardiac tissue, e.g., posterior leaflet and/or posterior annulus, and preferably not contact cardiac tissue, e.g., not contact the cardiac valve, not contact cardiac valve leaflets, not contact cardiac valve annulus, not contact chordae tendineae, and/or not contact cardiac chamber walls. Lower portion 23 may be sized and shaped to be positioned within the left ventricle without interfering with native chordae tendineae.

Membrane 20 may have a curved shape from upper portion 21 to intermediate portion 22 to lower portion 23. For example, membrane 20 may be curved in the second flowpath plane FP2 such that upper portion 21 and lower portion 23 curve around a native leaflet, e.g., posterior leaflet. For example, first surface 24 from upper portion 21 to intermediate portion 22 to lower portion 23 may have a concave shape and second surface 25 from upper portion 21 to intermediate portion 22 to lower portion 23 may have a convex shape. Membrane 20 may, for example, have a C-shape and/or a crescent-shape in the second flowpath plane FP2. In this regard, membrane 20 may have intersecting curved shapes. For example, membrane 20 may have a C-shape and/or a crescent-shape in the cardiac valve plane CVP that intersects with a C-shape and/or a crescent-shape in the second flowpath plane FP2. In one embodiment, membrane 20 forms a saddle-shaped structure.

Advantageously, the curved shape of upper portion 21 may be configured to be disposed upstream of the defective cardiac valve, so as prevent one or more native leaflets from ballooning or prolapsing during backflow and to prevent prosthetic device 10 migration. In one embodiment, upper portion 21 is curved to minimize ballooning or prolapse of the native posterior leaflet into the left atrium. The curved shape of lower portion 23 may be adapted to guide the native leaflet, e.g., posterior leaflet, to intermediate portion 22 during the cardiac cycle such that the native cardiac leaflets coapt with opposing surfaces of membrane 20 to reduce cardiac valve regurgitation.

Membrane 20 may include one or shaping bands configured to create and maintain curved shapes of membrane 20. Illustratively, membrane 20 includes shaping band 26 and shaping band 27 in intermediate portion 22.

Membrane 20 preferably comprises treated animal tissue, such as porcine, bovine, or equine pericardial tissue fixed using glutaraldehyde as is per se known in the art of prosthetic valve design. Alternatively, membrane 20 may comprise any of a number of synthetic fabrics, such as a polyethylene terephthalate fabric, e.g., DACRON™ (a registered trademark of Invista North America S.A.R.L. Corporation). As a further alternative, portions of membrane 20 may comprise synthetic material, while other portions may comprise animal tissue.

FIG. 3B illustrates exemplary expandable frame 30 of FIG. 3A. Expandable frame 30 may include upper portion 31, intermediate portion 32, lower portion 33, first attachment portion 40, and second attachment portion 41. Expandable frame 30 may be configured for implantation in a circular-shaped or oval-shaped cardiac valve and may comprise a superelastic material, such as a nickel-titanium alloy. The superelastic material may be treated to expand from a contracted delivery state to an expanded deployed state as is well-known in the art for such materials. Alternatively, expandable frame 30 may comprise non-superelastic metal alloy, such as stainless steel or cobalt-chrome alloy, that may be compressed onto a balloon catheter and then plastically expanded during deployment. Expandable frame 30 may be fully or partially covered with a material, e.g., membrane 20, made from treated animal tissue or any of a number of synthetic fabrics using sutures or biocompatible adhesive.

Upper portion 31 of expandable frame 30 is adapted to be coupled to upper portion 21 of membrane 20 to help shape membrane 20. Like upper portion 21 of membrane 20, upper portion 31 of expandable frame 30 may be adapted to extend into a heart lumen or chamber, e.g., left atrium, and may not contact cardiac tissue when deployed, e.g., not contact the cardiac valve, not contact cardiac valve leaflets, not contact cardiac valve annulus, not contact cardiac vessel walls, and/or not contact cardiac chamber walls. Some or all of upper portion 31 may curve toward cardiac tissue when deployed. For example, upper portion 31 may curve around a native leaflet, e.g., posterior leaflet, and toward a native annulus of the native leaflet, e.g., posterior annulus. In one embodiment, upper portion 31 is shaped in a loop which forms an upper lip adapted to hang over native cardiac tissue, e.g., posterior leaflet and/or posterior annulus, and preferably not contact cardiac tissue, e.g., not contact the cardiac valve, not contact cardiac valve leaflets, not contact cardiac valve annulus, not contact cardiac vessel walls, and/or not contact cardiac chamber walls. Upper portion 31 may include strain relief member 34 configured to permit deflection of expandable frame 30 to reduce strain during compression of the heart. Strain relief member 34 may bend inward under forward blood flow, thereby improving the transprosthetic gradient, and outward during retrograde blood flow, improving coaptation of membrane 20 with the opposing corresponding native cardiac leaflets. Strain relief member 34 may be used to control expansion of prosthetic device 10 as device 10 is exposed from the delivery catheter. Preferably, strain relief member 34 is made of a radiopaque material to permit visualization of prosthetic device 10 during implantation. Strain relief member 34 also may be used to anchor prosthetic device 10 to cardiac tissue by, for example, coupling strain relief member 34 to cardiac tissue, e.g., valve annulus, with a fixation device, e.g., a suture looped therethrough. Illustratively, strain relief member 34 comprises an eyelet positioned in the center of upper portion 31.

Intermediate portion 32 of expandable frame 30 is adapted to be coupled to intermediate portion 22 of membrane 20 to help shape membrane 20. Like intermediate portion 22 of membrane 20, intermediate portion 32 of expandable frame 30 is adapted to be deployed at the cardiac valve in between the native cardiac leaflets. Preferably, at least some of intermediate portion 32 is positioned in the cardiac valve plane CVP. Intermediate portion 32 may be adapted to contact cardiac tissue, e.g., commissures of the cardiac valve, when deployed. Intermediate portion 32 may include first and second posts 35 at opposing sides of intermediate portion 32. Posts 35 may be sized and shaped to contact cardiac tissue, e.g., antero-lateral commissure and/or postero-medial commissure, when deployed and may assist with securing prosthetic device 10 in a desired location at the cardiac valve.

Lower portion 33 of expandable frame 30 is adapted to be coupled to lower portion 23 of membrane 20 to help shape membrane 20. Like lower portion 23 of membrane 20, lower portion 33 of expandable frame 30 may be adapted to extend into another heart lumen or chamber, e.g., left ventricle, and may not contact cardiac tissue when deployed, e.g., not contact the cardiac valve, not contact cardiac valve leaflets, not contact cardiac valve annulus, not contact cardiac vessel walls, not contact chordae tendineae, and/or not contact cardiac chamber walls. Some or all of lower portion 33 may curve toward cardiac tissue, e.g., posterior leaflet, anterior leaflet, posterior annulus, and/or anterior annulus, when deployed. Illustratively, lower portion 33 includes first section 36 and second section 37. First section 36 may continue at the same angle as where lower portion 33 extends from intermediate portion 32. Second section 37 is angled in a different direction than first section 36 and preferably bifurcates a predetermined distance from where lower portion 33 extends from intermediate portion 32. For example, first section 36 may curve around a native leaflet, e.g., posterior leaflet, and toward a native annulus of the native leaflet, e.g., posterior annulus, while second section 37 may curve around another native leaflet, e.g., anterior leaflet, and toward an opposing portion of the annulus, e.g., anterior annulus. Lower portion 33 may have a compound angle to define first section 36, e.g., in the first flowpath plane FP1. The compound angle may cause first section 36 to have a more constricted angle to permit first section 36 to be positioned beneath the native leaflet, e.g., posterior leaflet, and between the bundles of chordae tendineae attached to the native leaflet. In one embodiment, first section 36 forms a triangular shape having a lower peak adapted to hang over native cardiac tissue, e.g., posterior leaflet and/or posterior annulus, and preferably not contact cardiac tissue, e.g., not contact the cardiac valve, not contact cardiac valve leaflets, not contact cardiac valve annulus, not contact cardiac vessel walls, not contact chordae tendineae, and/or not contact cardiac chamber walls. Similarly, second section 37 may form a triangular shape having a lower peak adapted to hang over native cardiac tissue, e.g., anterior leaflet and/or anterior annulus, and preferably not contact cardiac tissue, e.g., not contact the cardiac valve, not contact cardiac valve leaflets, not contact cardiac valve annulus, not contact cardiac vessel walls, not contact chordae tendineae, and/or not contact cardiac chamber walls. Second section 37 may also have a more constricted angle, the same or different constricted angle as first section 36, to permit second section 37 to be positioned beneath the native leaflet, e.g., anterior leaflet, and between the bundles of chordae tendineae attached to the native leaflet. First section 36 and second section 37 are preferably sized and shaped to be positioned within the left ventricle without interfering with native chordae tendineae. Illustratively, membrane 20 is coupled to first section 36, but not second section 37. In alternative embodiments, membrane 20 may be coupled to first section 36 and second section 37.

Lower portion 33 may include one or more strain relief members configured to permit deflection of expandable frame 30 to reduce strain during compression of the heart. Illustratively, first section 36 includes strain relief member 38 and second section 37 includes strain relief member 39. Strain relief members 38 and 39 may bend inward under forward blood flow, thereby improving the transprosthetic gradient, and outward during retrograde blood flow, improving coaptation of membrane 20 with the opposing corresponding native cardiac leaflets. Strain relief members 38 and 39 may be used to control expansion of prosthetic device 10 as device 10 is exposed from the delivery catheter. Preferably, strain relief members 38 and 39 are made of a radiopaque material to permit visualization of prosthetic device 10 during implantation. Strain relief members 38 and 39 also may be used to anchor prosthetic device 10 to cardiac tissue by, for example, coupling strain relief members 38 and 39 to cardiac tissue, e.g., valve annulus, with a fixation device, e.g., a suture looped therethrough. Illustratively, strain relief members 38 and 39 each comprises an eyelet positioned in the center of first section 36 and second section 37, respectively.

Attachment portions 40 and 41 may be adapted for securing prosthetic device 10 to cardiac tissue when deployed. Attachment portions 40 and 41 may be configured to engage predetermined region(s) or surface(s) within a patient's heart (such as the commissural areas of the defective cardiac valve, one or more leaflets of the valve, one or more portions of the annulus of the valve, and/or one or more heart chamber walls) to anchor prosthetic device 10 at a desired location within the native valve structure. Attachment portions 40 and 41 may extend away from opposing sides of expandable frame 30. For example, attachment portions 40 may extend from intermediate portion 32, e.g., at post 35, while attachment portion 41 extends from the opposing side of intermediate portion 32, e.g., at the other post 35. Beneficially, attachment portions 40 and 41 may be used to firmly anchor prosthetic device 10 within the native cardiac valve and may flex with the motion of the native valve to reduce the risk of device migration. Attachment portions 40 and 41 may be coated with a material such as animal tissue (e.g., porcine, bovine, or equine pericardial tissue) and/or any of a number of synthetic fabrics, such as a polyethylene terephthalate fabric, e.g., DACRON™ (a registered trademark of Invista North America S.A.R.L. Corporation) fixed using glutaraldehyde as is per se known in the art of prosthetic valve design. Attachment portions 40 and 41 may be fixed to cardiac tissue using a fixation device, e.g., sutures, pins, staples, or the like. For example, the fixation device may pierce the coating material to couple the coating material to cardiac tissue at the valve, valve annulus, valve leaflet(s), and/or heart chamber wall(s). Preferably, attachment portion 40 is adapted to be secured to cardiac tissue via one or more fixation devices configured to perforate the coating material and the cardiac valve annulus to couple attachment portion 40 to the annulus and attachment portion 41 is adapted to be secured to cardiac tissue via one or more fixation devices configured to perforate the coating material and the opposing side of the cardiac valve annulus to couple attachment portion 41 to the opposing side of the annulus. Attachment portion 40 may be curved in the shape of a portion of the valve annulus while attachment portion 41 is curved in the shape of an opposing portion of the valve annulus.

In one embodiment, attachment portions 40 and 41 may be adapted to loop upwardly to contact walls within the left atrium to anchor prosthetic device 10 within the mitral valve. For example, attachment portions 40 and 41 may be shaped similar to the anchoring loops of U.S. Patent Publication No. 2006/0058871 to Zakay, the entire contents of which are incorporated herein by reference.

Attachment portions 40 and 41 may each include multiple components. For example, attachment portion 40 may include first medial section 42 and second medial section 43 and attachment portion 41 may include first lateral section 44 and section lateral section 45. First medial section 42 and second medial section 43 may be curved in the shape of a portion of the valve annulus, e.g., portion adjacent the postero-medial commissure PMC. For example, second medial section 43 may be banana-shaped and adapted to be coupled to the mitral valve annulus. Preferably, second medial section 43 is adapted to sit at least partially over P3 of the mitral valve MV on the left atrium side. First medial section 42 may be a loop that extends in a generally opposing direction from second medial section 43, which may also be a loop. First medial section 42 may be adapted to contact the cardiac valve annulus to prevent movement or tilting of prosthetic device 10 after deployment. Second medial section 43 may be adapted to be secured to cardiac tissue via one or more fixation devices configured to perforate coating material covering second medial section 43 and perforate the cardiac valve annulus to couple second medial section 43 to the annulus. An additional fixation device(s) may be used to couple first medial section 42 to the annulus, although, preferably, such fixation device is not needed.

First lateral section 44 and second lateral section 45 may be curved in the shape of an opposing portion of the valve annulus, e.g., portion adjacent the antero-lateral commissure ALC. For example, second lateral section 45 may be banana-shaped and adapted to be coupled to the mitral valve annulus. Preferably, second lateral section 45 is adapted to sit at least partially over P1 of the mitral valve MV on the left atrium side. First lateral section 44 may be a loop that extends in a generally opposing direction from second lateral section 45, which may also be a loop. First lateral section 44 may be adapted to contact the cardiac valve annulus to prevent movement or tilting of prosthetic device 10 after deployment. Second lateral section 45 may be adapted to be secured to cardiac tissue via one or more fixation devices configured to perforate coating material covering second lateral section 45 and perforate the cardiac valve annulus to couple second lateral section 45 to the annulus. An additional fixation device(s) may be used to couple first lateral section 44 to the annulus, although, preferably, such fixation device is not needed.

Preferably, prosthetic device 10 is configured such that membrane 20 coapts with, and improves function of, one or more native leaflets of the defective cardiac valve, for example, during backpressure. In one embodiment, membrane 20 is adapted to occupy a certain amount of space within the central opening of the native cardiac valve. Advantageously, prosthetic device 10 works together with the native cardiac valve, rather than pushing the leaflets of the native cardiac valve aside and rending the native valve structures ineffective. Additionally, membrane 20 is shaped in a sufficiently thin manner so as to reduce the risk of obstructing blood flow through the cardiac valve.

Advantageously, membrane 20 need not include a pocket or plug. Such pockets or plugs have been shown to expand too quickly during the cardiac cycle, thereby interfering with native cardiac leaflets. In addition, the pocket/plug receives blood at high pressures, making the prosthetic prone to dislodgement after implantation. Also, the pocket/plug creates a risk that thrombus will build up in the pocket/plug, causing harmful effects if released into the bloodstream such as a stroke.

Figure 1:
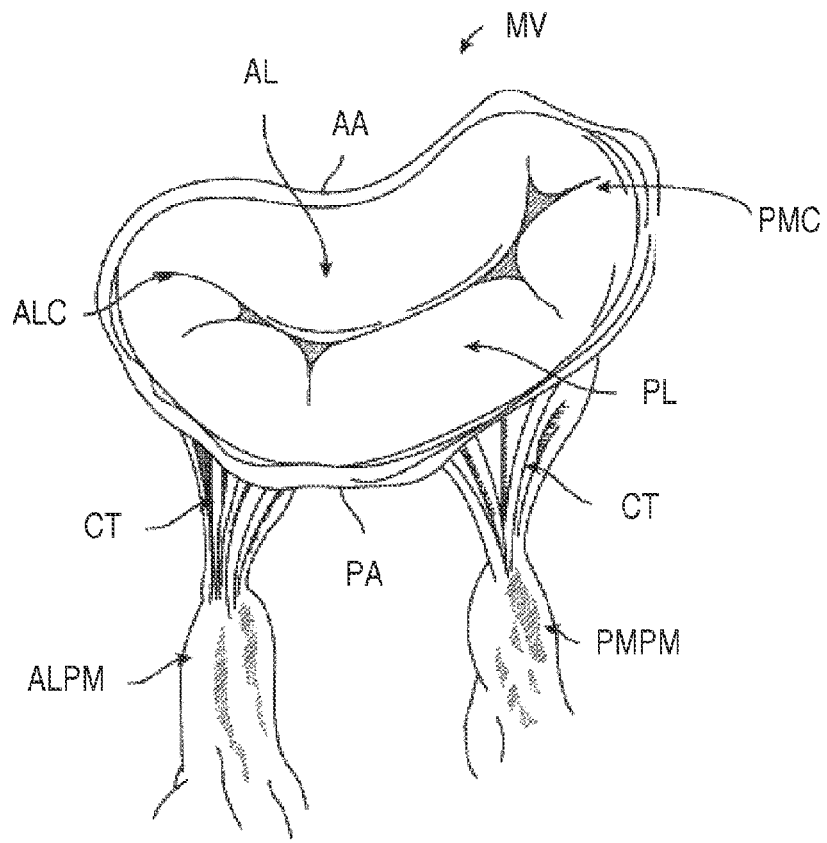
FIG. 1 illustrates the anatomy of a mitral valve.
Figure 2A:
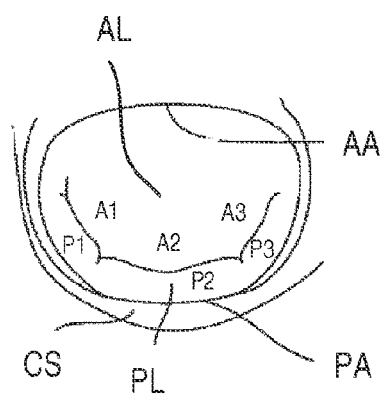
FIGS. 2A and 2B illustrate the anatomy of a mitral valve, where FIG. 2B includes representative planes used solely for explanatory purposes herein.
Figure 2B:
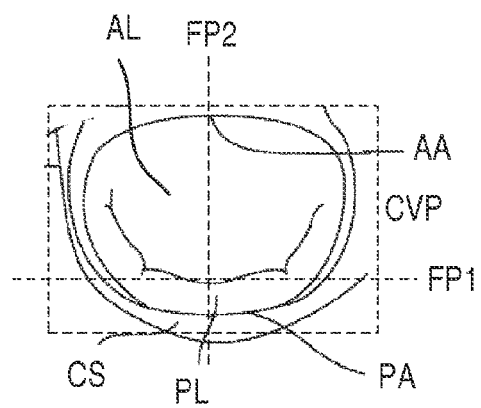
Figures 4, 5:
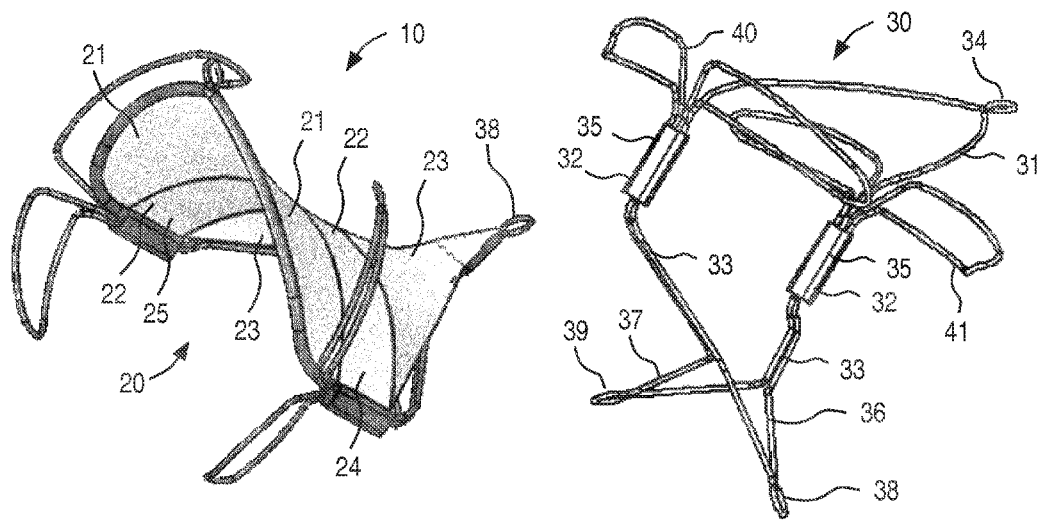
FIG. 4 is another perspective view of the exemplary prosthetic device viewed at a different angle than FIG. 1.
FIG. 5 is another perspective view of the exemplary expandable frame viewed at a different angle than FIG. 3B.

FIG. 4 is another perspective view of prosthetic device 10 viewed at a different angle than FIG. 1. FIG. 5 is another perspective view of expandable frame 30 viewed at a different angle than FIG. 3B.

Figure 6A:
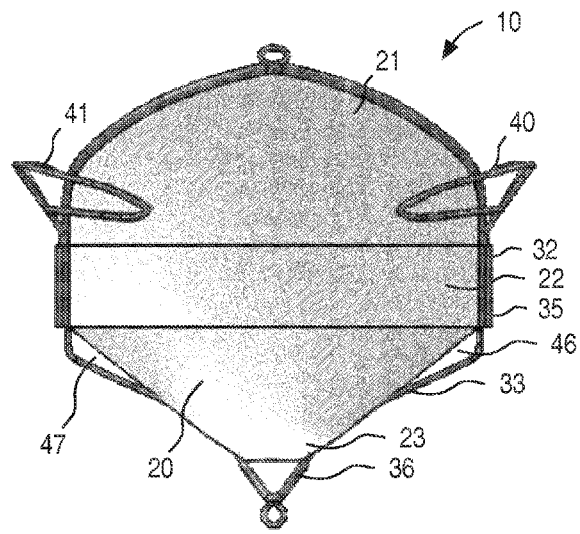
FIGS. 6A and 6B are, respectively, front views of the exemplary prosthetic device and the exemplary expandable frame.
Figure 6B:
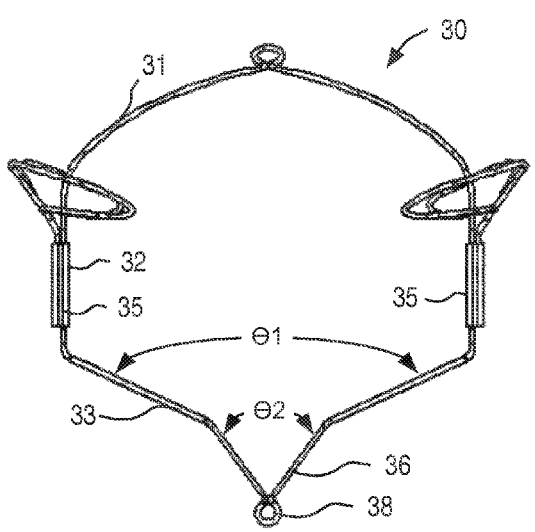
Figure 7:
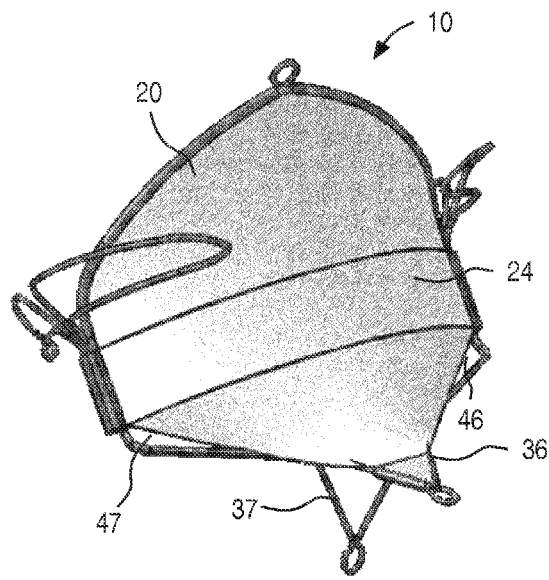
FIGS. 7 and 8 are additional perspective views of the exemplary prosthetic device viewed at different angles than FIG. 1.
Figure 8:
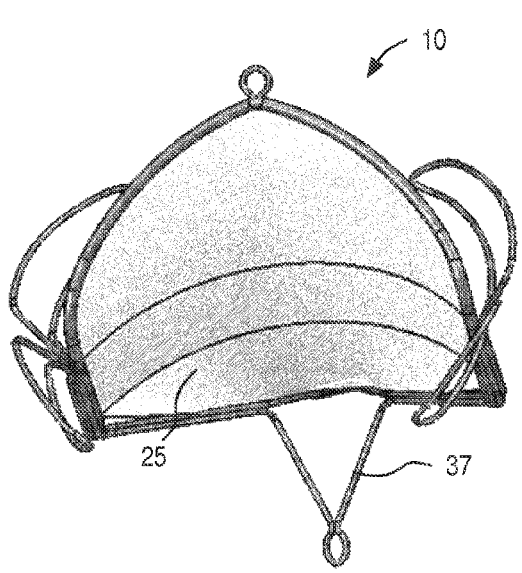

FIGS. 6A and 6B are, respectively, front views of prosthetic device 10 and expandable frame 30. FIGS. 7 and 8 are additional perspective views of prosthetic device 10 viewed at different angles than FIG. 1. As best shown in FIGS. 6A and 7, membrane 20 may not be coupled to expandable frame 30 at certain portions of the frame. For example, membrane 20 is illustratively not coupled to second section 37 of lower portion 33 and not coupled in exposed portions 46 and 47. Exposed portions 46 and 47 may each be defined where membrane 20 decouples from expandable frame 30 at intermediate portion 32 (e.g., below posts 35) to where membrane 20 recouples to expandable frame 30 at lower portion 33 (e.g., above first and second sections 36 and 37). Exposed portions 46 and 47 may be sized to reduce or eliminate contact between prosthetic device 10, e.g., specifically lower portions 23 and 33, and native chordae tendineae. Exposed portions 46 and 47 also permit blood flow therethrough, e.g., to improve blood flow at the posterior side of the outflow track from the left atrium to the left ventricle.

Referring now to FIG. 6B, lower portion 33 may be defined by a compound angle, e.g., in the first flowpath plane FP1 and/or in the second flowpath plane FP2. The compound angle may cause first section 36 to have a more constricted angle to permit first section 36 to be positioned beneath the native leaflet, e.g., posterior leaflet, and between the bundles of chordae tendineae attached to the native leaflet. The compound angle may also cause second section 37 to have a more constricted angle, the same or different constricted angle as first section 36, to permit second section 37 to be positioned beneath the native leaflet, e.g., anterior leaflet, and between the bundles of chordae tendineae attached to the native leaflet. The compound angle may further cause second section 37 to bifurcate a predetermined distance from where lower portion 33 extends from intermediate portion 32 to permit second section 37 to be positioned beneath the native leaflet, e.g., anterior leaflet, and between the bundles of chordae tendineae attached to the native leaflet. Lower portion 33 may extend from opposing sides of intermediate portion 32 and may angle a predetermined angle Θ1 toward one another, e.g., in the first flowpath plane FP1. The predetermined angle Θ1 may be, for example, between 60 to 150°, between 60 to 120°, between 80 to 150°, between 90 to 150°, between 90 to 120°, between 100 to 140°, or the like. Opposing sides of first section 36 may angle a predetermined angle Θ2 toward one another, e.g., in the first flowpath plane FP1. Preferably, the predetermined angle Θ2 is less than the predetermined angle Θ1 to facilitate positioning beneath the native leaflet, e.g., posterior leaflet, and between the bundles of chordae tendineae attached to the native leaflet. The predetermined angle Θ2 may be, for example, between 10 to 100°, between 20 to 100°, between 30 to 90°, between 40 to 90°, between 50 to 90°, between 60 to 90°, between 60 to 80°, between 60 to 70°, or the like. Opposing sides of second section 37 may angle the predetermined angle Θ2 toward one another, e.g., in the first flowpath plane FP1, or a different predetermined angle than θ2. Preferably, the predetermined angle for second section 37 is less than the predetermined angle Θ1 to facilitate positioning beneath the native leaflet, e.g., anterior leaflet, and between the bundles of chordae tendineae attached to the native leaflet.

FIGS. 9A and 9B are, respectively, side views of prosthetic device 10 and expandable frame 30. FIGS. 10A and 10B are, respectively, top views of prosthetic device 10 and expandable frame 30.

Referring to FIG. 9A, prosthetic device 10 may be adapted for implantation at least partially within the cardiac valve plane CVP (e.g., mitral valve plane). Illustratively, the cardiac valve plane CVP runs through intermediate portion 32 below attachment portions 40 and 41 such that attachment portions may be secured to the valve annulus. Preferably, attachment portions 40 and 41 contact the mitral valve annulus in the left atrium side of the mitral valve. Upper portion 31 is angled a predetermined angle Θ3 from the cardiac valve plane CVP. The predetermined angle Θ3 may be, for example, between 10 to 80°, between 10 to 70°, between 10 to 60°, between 10 to 50°, between 10 to 45°, between 20 to 50°, or the like. The apex of upper portion 31 may be a predetermined distance X from intermediate portion 32. The predetermined distance X may be selected to permit upper portion 31 to hang over the native cardiac leaflet and/or annulus. The predetermined distance X may be, for example, between 4 to 20 mm, between 4 to 17 mm, between 4 to 15 mm, between 5 to 12 mm, between 5 to 10 mm, or the like. The apex of lower portion 33 also may be a predetermined distance from intermediate portion 32. The predetermined distance may be the same predetermined distance X as the apex of upper portion 31, as illustrated, or may be a different predetermined distance. The predetermined distance may be selected to permit lower portion 33 to hang over the native cardiac leaflet and/or annulus.

The valley of intermediate portion 22 at first surface 24 in the first flowpath plane FP1, which also may be approximately the apex of first surface 24 in the cardiac valve plane CVP, may be a predetermined distance Y from intermediate portion 32. The predetermined distance Y may be selected to permit first surface 24 to abut the native cardiac leaflet, e.g., posterior leaflet, during systole and second surface 25 to abut another native cardiac leaflet, e.g., anterior leaflet, during systole. Preferably, the predetermined distance Y is less than the predetermined distance X to permit the upper and lower portions of the membrane to hang over the native cardiac leaflet at least during systole. The predetermined distance Y may be, for example, between 4 to 15 mm, between 4 to 14 mm, between 4 to 13 mm, between 4 to 12 mm, between 5 to 12 mm, between 6 to 12 mm, between 7 to 12 mm, between 8 to 12 mm, between 5 to 10 mm, or the like.

Lower portion 33 is angled a predetermined angle Θ4 from the cardiac valve plane CVP. The predetermined angle Θ4 may be the same angle or a different angle than predetermined angle Θ3. The predetermined angle Θ4 may be, for example, between 10 to 80°, between 10 to 70°, between 10 to 60°, between 10 to 50°, between 10 to 45°, between 20 to 50°, or the like. First section 36 is preferably angled at the same predetermined angle Θ4 as the upper part of lower portion 33. Second section 37 may branch off from first section 36 at a predetermined angle Θ5. The predetermined angle Θ5 may be, for example, between 30 to 120°, between 40 to 100°, between 60 to 100°, between 70 to 100°, between 80 to 90°, about 90°, or the like. Preferably, second section 37 bifurcates a predetermined distance from where lower portion 33 extends from intermediate portion 32. Second section 37 may bifurcate a predetermined distance Z from the cardiac valve plane CVP. The predetermined distance Z is preferably selected to permit second section 37 to be positioned beneath the native leaflet, e.g., anterior leaflet, and between the bundles of chordae tendineae attached to the native leaflet. The predetermined distance Z may be, for example, between 5 to 25 mm, between 10 to 25 mm, between 10 to 20 mm, between 12 to 20 mm, between 15 to 25 mm, between 15 to 20 mm, or the like.

Figure 11A:
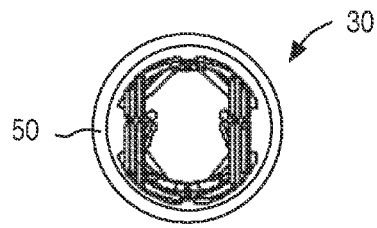
FIGS. 11A-11D depict illustrative embodiments of a catheter for transvascular delivery of the prosthetic device of the present disclosure, wherein the expandable frame is shown in a contracted delivery state.
Figure 11B:
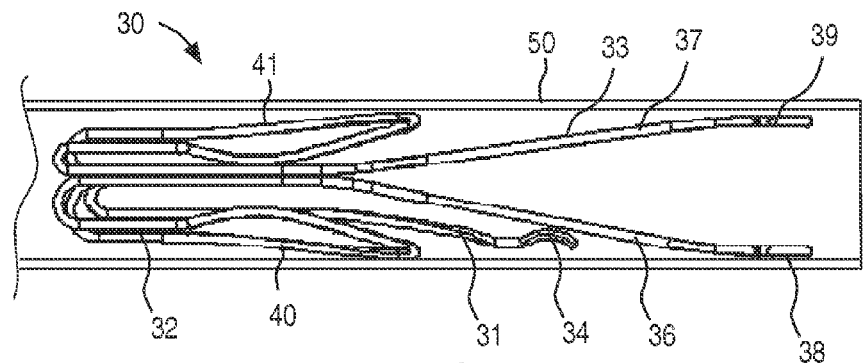
Figure 11C:
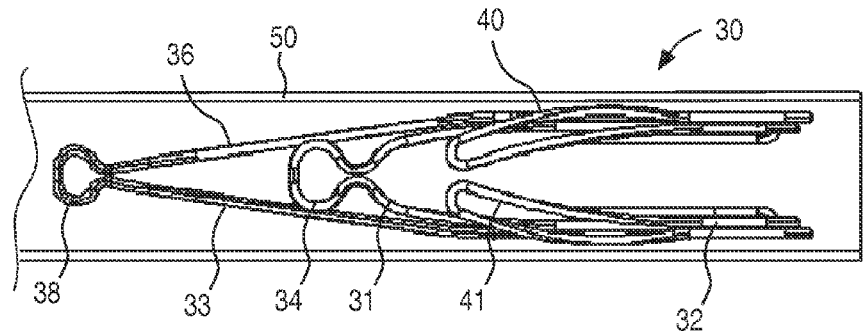
Figure 11D:
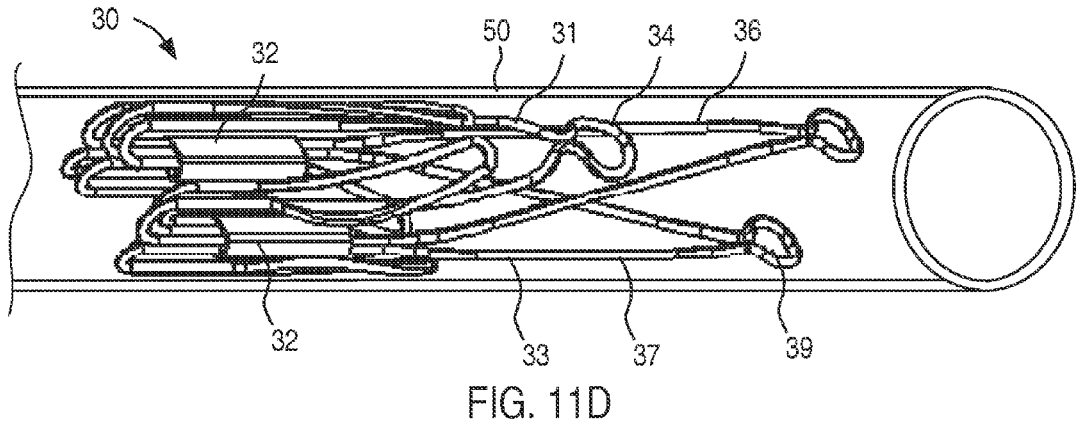

Referring now to FIGS. 11A to 11D, an exemplary embodiment of a delivery catheter for delivering the prosthetic device of the present disclosure is described. Delivery catheter 50 includes a suitable length of tubing having a distal end, a proximal end, an internal lumen extending therebetween. Delivery catheter 50 is configured to deliver prosthetic device 10 to a cardiac valve for implantation. Accordingly, delivery catheter 50 and its internal lumen are sized and shaped to receive and maintain prosthetic device 10 in a contracted delivery state. The internal lumen of delivery catheter 50 also may be sized to receive a guidewire or may include a separate guidewire lumen to accommodate passage of a guidewire for over-the-wire or rapid exchange delivery. For clarity, FIGS. 11A to 11D show the prosthetic device with only expandable frame 30, and without the membrane, in the contracted delivery state. In FIGS. 11B and 11D, expandable frame 30 is disposed in delivery catheter 50 with lower portion 33 of expandable frame 30 closest to the distal end of delivery catheter 50 to facilitate delivery to the mitral valve MV via the left atrium LA while FIG. 11C depicts upper portion 31 and/or intermediate portion 32 closer to the distal end of delivery catheter 50 than lower portion 33 to facilitate delivery to the mitral valve MV via the left ventricle LV.

Delivery catheter 50 preferably comprises materials conventionally used in catheter designs, and has lengths and profiles suitable for the selected access path, i.e., either transvascular or transapical. Prosthetic device 10 may be crimped down to the contracted delivery state by folding upper portion 31 over intermediate portion 32 such that upper portion 31 is adjacent to lower portion 33. In addition, attachment portions 40 and 41 may be folded down to be adjacent to upper portion 31 and/or lower portion 33. In one embodiment, expandable frame 30 is self-expanding and causes prosthetic device 10 to expand when deployed. In an alternative embodiment, such as for plastically deformable embodiments of expandable frame 30, a catheter having an expandable balloon or mandrel configured, as is conventional in the art of balloon-catheters, to be inflated may be deployed through delivery catheter 50 or separately to cause prosthetic device 10 to expand when deployed.

Figure 12:
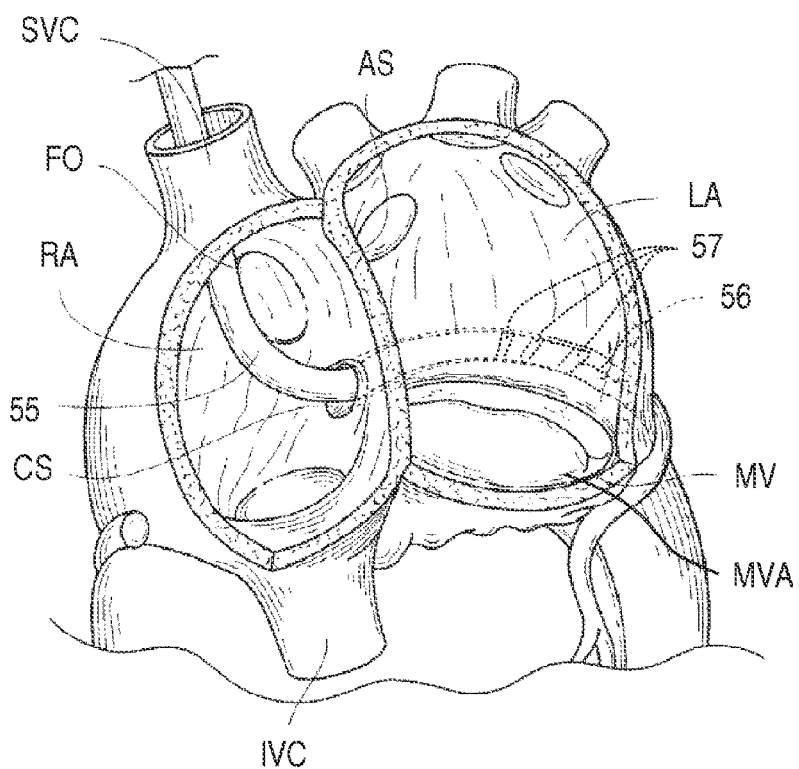
FIGS. 12 and 13 are illustrative views showing catheters for use in deploying the prosthetic device of present disclosure for repairing a defective mitral valve.
Figure 13:
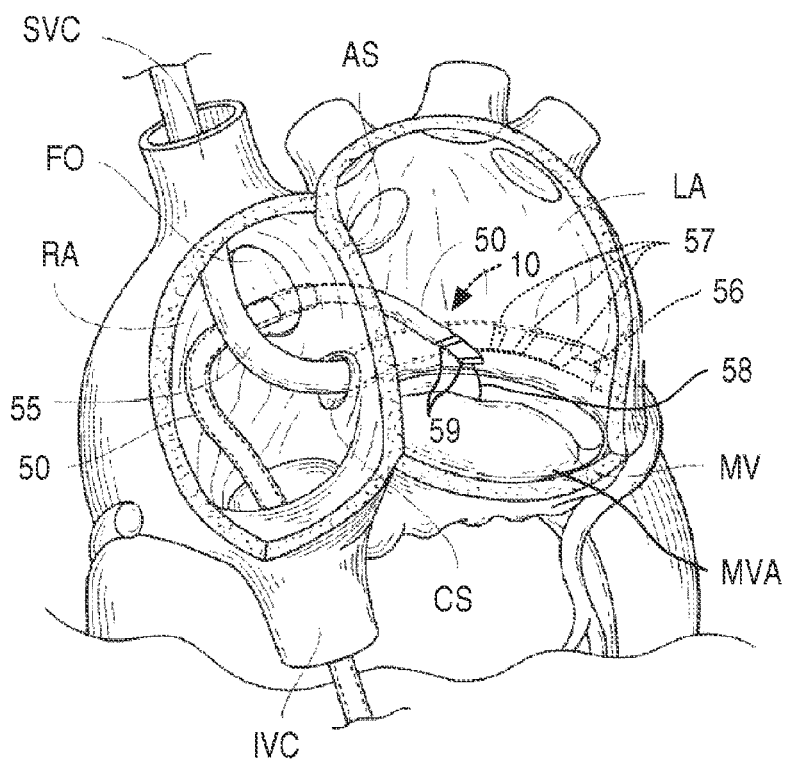

Referring to FIGS. 12 and 13, a method of deploying the prosthetic device of present disclosure is now described in the context of repairing a defective mitral valve. In FIGS. 12 and 13, a human heart is shown having a mitral valve MV, a mitral valve annulus MVA, a left atrium LA, an atrial septum AS, a superior vena cava SVC, a fossa ovalis FO, a right atrium RA, a coronary sinus CS, and an inferior vena cava IVC.

As shown in FIG. 12, visualization catheter 55 may be introduced into the coronary sinus CS transvascularly, e.g., via the superior vena cava SVC. Visualization catheter 55 may be inserted over guidewire 56 that had been previous introduced into the coronary sinus CS. Visualization catheter 55 may include one or more radiopaque markers 57 aligned at the distal portion of visualization catheter 55 to permit visualization, e.g., using fluoroscopy, 2D or 3D ultrasound, computed tomography, magnetic resonance, or combinations thereof. Deployment of visualization catheter 55 within the coronary sinus CS such that radiopaque markers 57 are adjacent to the mitral valve annulus MVA may be used to permit visualization of the position of the mitral valve annulus MVA during implantation of prosthetic device 10. Preferably, fluoroscopy and 3D ultrasound are used in combination during the implantation procedure.

Referring to FIG. 13, after deployment of visualization catheter 55 within the coronary sinus CS, delivery catheter 50, having prosthetic device 10 disposed therein, may be introduced into the patient's vasculature. Delivery catheter 50 may be introduced over guidewire 58. Guidewire 58 may be inserted antegrade through the femoral vein, into the right atrium RA via the inferior vena cava IVC, and perforate the atrial septum AS, e.g., at the fossa ovalis FO, to access the left atrium LA. The distal end of guidewire 58 may be advanced between the anterior and posterior leaflets of the mitral valve MV and into the left ventricle LV. Delivery catheter 50 is inserted, e.g., over guidewire 58 if previously inserted, antegrade through the femoral vein, into the right atrium RA via the inferior vena cava IVC, and perforates the atrial septum AS, e.g., at the fossa ovalis FO, to access the left atrium LA. The distal end of delivery catheter 50 may be advanced between the anterior and posterior leaflets of the mitral valve MV and into the left ventricle LV. Delivery catheter 50 may include may include one or more radiopaque markers 59 aligned at the distal portion of delivery catheter 50 to permit visualization, e.g., using fluoroscopy, 2D or 3D ultrasound, computed tomography, magnetic resonance, or combinations thereof.

Once delivery catheter 50 is disposed partially through the mitral valve MV in a suitable position, as may be determined using visualization of radiopaque markers 57 and/or 59, delivery catheter 50 is retracted proximally while maintaining prosthetic device 10 between the anterior and posterior leaflets of the mitral valve MV. Prosthetic device 10 may be maintained in place using, for example, another catheter disposed within delivery catheter 50 that contacts prosthetic device 10 and is held in place while delivery catheter 50 is withdrawn. Alternatively, or additionally, prosthetic device 10 may be coupled to sutures or control wires, e.g., looped through eyelet 34, 38, and/or 39, which may be released by pulling proximally until each suture/control wire is no longer looped around prosthetic device 10 or may be cut using a suitable transvascular tool. Delivery catheter 50 may be rotated and moved proximally and distally, e.g., by moving and/or rotating a handle of delivery catheter 50, to properly align attachment portions 40 and 41 of prosthetic device 10 with the predetermined region, e.g., resting on the atrial side of the mitral valve annulus MVA, of the mitral valve MV, e.g., using visualization. As prosthetic device 10 is exposed out of the distal end of delivery catheter 50, prosthetic device 10 may expand so that the membrane is deployed within the flow path circumscribed by the native leaflets and occupies at least a portion of the central opening of the mitral valve MV. Preferably, upper portions 21 and 31 are disposed in the left atrium LA, intermediate portions 22 and 32 are disposed at least partially within the mitral valve MV, and the lower portions 23 and 33 are disposed in the left ventricle LV.

Referring to FIGS. 14A and 14B, optional apparatus and methods for further anchoring prosthetic device 10 to cardiac tissue are described. After implanting prosthetic device 10 within the desired cardiac valve, fixation catheter 60 carrying one or more fixation devices 61 may be deployed. Fixation device 61 illustratively includes body portion 62 coupled to rotating portion 63 via hinge 64. Rotating portion 63 may include piercing end 65 configured to pierce cardiac tissue. Fixation device 61 may be coupled to wire 66 via coupling portion 67. Wire 66 may be a rigid wire or a flexible suture and coupling portion 67 may be an eyelet configured to receive wire or a fatigue area configured to break under force. Fixation device 61 may be loaded into fixation catheter 60 in a substantially linear contracted delivery state as shown in FIG. 14A and may transition to a deployed anchoring state as shown in FIG. 14B.

Fixation catheter 60 may be introduced through the femoral artery and proceed retrograde to the left ventricle LV. Fixation catheter 60 is positioned at the mitral valve MV on the left ventricle LV side, e.g., by visualizing radiopaque markers on fixation catheter 60, and the mitral valve MV is perforated, preferably at the mitral valve annulus MVA. The mitral valve MV may be perforated by advancing fixation device 61 distally such that piercing end 65 pierces the mitral valve, e.g., at the mitral valve annulus MVA. Alternatively, the mitral valve annulus MVA may be perforated by a radio frequency emitter on or in fixation catheter 60. Fixation device 61 is moved distally through the perforation in the mitral valve MV, e.g., in about the middle of P1, and perforates prosthetic device 10, preferably at attachment portion 40 and more preferably through second medial section 43 until all of rotating portion 63 has passed through attachment portion 40 and is in the left atrium LA. The perforation of the annulus may be done whilst orienting fixation catheter 60. Rotating portion 63 may self-rotate on hinge 64 or may rotate responsive to pulling fixation device 61 proximally so as to be substantially perpendicular with body portion 62 to create a T-shape as shown in FIG. 14B. Clip 68 may be inserted over wire 66 to contact the mitral valve MV on the left ventricle side LV to further secure fixation device 61. Then, wire 66 may be decoupled from fixation device 61 via release of coupling portion 67, e.g., by pulling with sufficient force, unlooping, or cutting.

During or after deployment of fixation device 61, fixation catheter 70 carrying one or more fixation devices may be deployed as shown in FIG. 15. Fixation devices within fixation catheter 70 may be the shape as fixation devices delivered within fixation catheter 60 or they may be different. Accordingly, fixation catheters 60 and 70 may deliver fixation devices 61 and/or 71. Like fixation device 61, fixation device 71 illustratively includes body portion 72 coupled to rotating portion 73 via hinge 74. However, fixation device 71 may include additional rotating portion 78 and hinge 79 to create an I-shape rather than a T-shape. Rotating portion 73 may include piercing end 75 configured to pierce cardiac tissue. Fixation device 71 may be coupled to wire 76 via coupling portion 77. Wire 76 may be a rigid wire or a flexible suture and coupling portion 77 may be an eyelet configured to receive wire or a fatigue area configured to break under force. Fixation device 71 may be loaded into fixation catheter 70 in a substantially linear contracted delivery state and may transition to a deployed anchoring state as shown in FIG. 15.

Fixation catheter 70 may be introduced through the femoral artery and proceed retrograde to the left ventricle LV. Fixation catheter 70 is positioned at the mitral valve MV on the left ventricle LV side, e.g., by visualizing radiopaque markers on fixation catheter 70, and the mitral valve MV is perforated, preferably at the mitral valve annulus MVA. The mitral valve MV may be perforated by advancing fixation device 71 distally such that piercing end 75 pierces the mitral valve, e.g., at the mitral valve annulus MVA. Alternatively, the mitral valve annulus MVA may be perforated by a radio frequency emitter on or in fixation catheter 70. Fixation device 71 is moved distally through the perforation in the mitral valve MV, e.g., in about the middle of P3, and perforates prosthetic device 10, preferably at attachment portion 41 and more preferably through second lateral section 45 until all of rotating portion 73 has passed through attachment portion 41 and is in the left atrium LA. The perforation of the annulus may be done whilst orienting fixation catheter 70. Rotating portions 73 and 78 may self-rotate on hinges 74 and 79, respectively, or may rotate responsive to pulling fixation device 71 proximally so as to be substantially perpendicular with body portion 72 to create an I-shape as shown in FIG. 15. Then, wire 76 may be decoupled from fixation device 71 via release of coupling portion 77, e.g., by pulling with sufficient force, unlooping, or cutting.

Delivery catheter 50, fixation catheter 60, and/or fixation catheter 70 are fully withdrawn leaving prosthetic device 10 deployed in the mitral valve, as depicted in FIGS. 16A and 16B. FIG. 16A shows the heart in systole where the anterior leaflet AL abuts a surface of the membrane and the posterior leaflet PL abuts an opposing surface of the membrane to more fully close the mitral valve, thereby treating cardiac valve regurgitation. The anterior leaflet AL and posterior leaflet PL of the mitral valve MV coapt against the expanded deployed prosthetic device 10; illustratively, against opposing surfaces of the membrane such that the membrane is suspended within the flow path defined by the leaflets AL and PL and the membrane coapts with, and improve functioning of, the leaflets AL and PL. FIG. 16B shows the heart in diastole where prosthetic device 10 permits blood flow through the mitral valve MV while occupying at least a portion of the central opening of the valve.

In an alternative embodiment, prosthetic device 10 may be implanted with delivery catheter 50 using a minimally-invasive approach wherein delivery catheter 50 is inserted through a keyhole opening in the chest and delivery catheter 50 is inserted transapically from below the mitral valve. As yet another alternative, an open heart surgery approach may be used to gain access to the mitral valve to implant prosthetic device 10. In an embodiment where prosthetic device 10 is implanted using an alternative transvascular approach, implantation of a mitral valve embodiment, for example, may be accomplished by passing delivery catheter 50 through the aorta, into the aortic valve AV and into the left ventricle LV to gain access to the mitral valve MV from below. In this embodiment, prosthetic device 10 may be loaded in delivery catheter 50 as depicted in FIG. 11C.

Referring to FIGS. 17A and 17B, a method for deploying a replacement valve prosthesis, such as are known in the art, within the deployed prosthetic device of the present disclosure is now described. Catheter 85 having the replacement valve disposed therein is advanced to the mitral valve MV under visualization from the left atrium as shown or from the left ventricle. The distal end of catheter 85 is positioned between attachment portions 40 and 41 of prosthetic device 10. Catheter 85 then is withdrawn and replacement valve prosthesis 80 expands and compresses prosthetic device 10 toward the mitral valve MV, as depicted in FIG. 17A. As replacement valve 80 expands, it preferably engages and anchors to prosthetic device 10. For example, expanding replacement valve 80 may cause attachment portions 40 and 41 to exert force on valve 80, thereby securing valve 80 within prosthetic device 10. Additionally, replacement valve 80 may be secured to prosthetic device 10 using, for example, sutures or biocompatible adhesive. In turn, because prosthetic device 10 is firmly anchored to the cardiac valve, e.g., mitral valve MV, replacement valve 80 is anchored at the cardiac valve.

Replacement valve 80 in FIG. 17A illustratively is constructed as described in U.S. Pat. No. 4,490,859 to Black et al., which is incorporated herein by reference, and/or the above-mentioned patents to Andersen et al., and comprises treated animal tissue, such as porcine, bovine or equine pericardial tissue, or any of a number of synthetic fabrics, such as a polyethylene terephthalate fabric, e.g., DACRON™ (a registered trademark of Invista North America S.A.R.L. Corporation), mounted on a collapsible metal alloy or polymer frame. Collapsible frame 81 may include two or more upstanding posts disposed on the sides of the frame to form commissural points for the tissue or synthetic fabric leaflets 82. As described in the foregoing patent, the tissue or fabric components of the valve body may be cut from flat pieces of material, and then sewn or bonded together, and to the upstanding posts and the frame, to form a valve that mimics the functionality of an intact non-diseased mitral valve.

Alternatively, the replacement prosthesis may be of any other construction suitable to be collapsed to a reduced diameter so as to permit the prosthetic valve to be delivered via catheter in a contracted delivery state. For example, replacement valve 90 in FIG. 17B is a self-expanding percutaneous replacement valve constructed as described in U.S. Pat. No. 7,914,569 to Nguyen, the entire contents of which are incorporated herein by reference. Replacement valve 90 may be a replacement valve constructed by Medtronic CoreValve LLC of Minneapolis, Minn. or by Edwards Lifesciences of Irvine, Calif. constructed in accordance with, for example, U.S. Pat. No. 8,002,825 to Letac, the entire contents of which are incorporated herein by reference. As replacement valve 90 expands from a delivery catheter, e.g., catheter 85, it preferably engages and anchors to prosthetic device 10. For example, expanding replacement valve 90 may cause attachment portions 40 and 41 to exert force on valve 90, thereby securing valve 90 within prosthetic device 10. Additionally, replacement valve 90 may be secured to prosthetic device 10 using, for example, sutures or biocompatible adhesive. In turn, because prosthetic device 10 is firmly anchored to the cardiac valve, e.g., mitral valve MV, replacement valve 90 is anchored at the cardiac valve.

Replacement valve 80 or 90 may be implanted immediately after prosthetic device 10 is deployed or may be implanted minutes, days, months, or years after prosthetic device 10 is deployed. In one embodiment, replacement valve 80 or 90 is implanted because a defective cardiac valve having prosthetic device 10 deployed thereon further degenerates, for example, due to disease progression or aging, such that valve replacement is required. Replacement valve 80 or 90 may be implanted using a transcatheter approach, a minimally invasive approach, or an open heart surgery approach.

As will be appreciated by one of ordinary skill, expandable frame 30 may comprise, for example, a suitably trained shape memory alloy, that expands to a deployed shape for use in a non-circular cardiac valve, such as an ovoid or D-shaped configuration. In this latter case, membrane 20 should be configured so that, when expandable frame 30 is fully deployed, the membrane expands to a predetermined shape with the required level of coaptation.

In accordance with an alternative embodiment of the present disclosure, expandable frame 30 may be loaded and deployed without membrane 20 in a manner similar to descriptions above with respect to FIGS. 12-16B. In this embodiment, attachment portions 40 and 41 apply outward force to the annulus, preferably at the commissures of the defective valve, to forcefully ovalize or modify the shape of the annulus to enhance leaflet coaptation and thereby reduce cardiac valve regurgitation.

* * *

While various illustrative embodiments are described above, it will be apparent to one skilled in the art that various changes and modifications may be made therein without departing from the invention. The appended claims are intended to cover all such changes and modifications that fall within the true scope of the invention.

What is claimed:

1. A prosthetic device for repairing a cardiac valve defining a flow path bounded by a first native leaflet and a second native leaflet, the prosthetic device comprising:
an expandable frame configured to transition from a contracted delivery state to an expanded deployed state, the expandable frame defining a saddle-shaped structure in the expanded deployed state, wherein the saddle-shaped structure has a long axis configured to extend through the cardiac valve so that an upper portion is disposed in a first heart chamber and a first lower portion is disposed in a second heart chamber, and a short axis, shorter than the long axis, the saddle-shaped structure having a curvature configured to conform to an annulus of the cardiac valve, the expandable frame having one or more attachment portions configured to secure the prosthetic device to cardiac tissue in the expanded deployed state; and
a membrane coupled to the expandable frame and adopting the saddle-shape when the expandable frame is in the expanded deployed state, the membrane defining a first surface and a second surface, the membrane configured to be suspended in the flow path so that the first surface is configured to abut the first native leaflet during systole but not during diastole and the second surface is configured to abut the second native leaflet during systole but not during diastole, to thereby reduce cardiac valve regurgitation.

2. The prosthetic device of claim 1, wherein the expandable frame further comprises a second lower portion that is configured to curve toward the second native leaflet.

3. The prosthetic device of claim 2, wherein the membrane is not coupled to at least part of the second lower portion to define an exposed portion configured to reduce or eliminate contact between the second lower portion and native chordae tendineae.

4. The prosthetic device of claim 2, wherein the first lower portion and the second lower portion each comprise a peak.

5. The prosthetic device of claim 1, wherein the membrane is coupled to the saddle-shaped structure along an entire perimeter of the membrane.

6. The prosthetic device of claim 1, wherein a convex portion of the first surface at a plane of the cardiac valve is sized and shaped to mimic a curve of the first native leaflet.

7. The prosthetic device of claim 1, wherein a concave portion of the second surface at a plane of the cardiac valve is sized and shaped to mimic a curve of the second native leaflet.

8. The prosthetic device of claim 1, wherein the expandable frame having the membrane coupled thereto is configured to be contracted to the contracted delivery state for loading and delivery with a delivery catheter.

9. The prosthetic device of claim 1, wherein the one or more attachment portions comprise first and second curved portions configured to engage opposing portions of the annulus of the cardiac valve.

10. The prosthetic device of claim 1, wherein the one or more attachment portions are configured to be secured to cardiac tissue via one or more fixation devices.

11. The prosthetic device of claim 1, wherein the expandable frame is configured to accommodate deployment of a replacement valve, such that the expandable frame serves as an anchor for the replacement valve.

12. The prosthetic device of claim 1, wherein the upper portion of the saddle-shaped structure curves around the first native leaflet for 4 to 17 mm.

13. The prosthetic device of claim 1, wherein the expandable frame further comprises one or more strain relief members configured to permit deflection of the expandable frame to reduce strain during compression of the heart.

14. The prosthetic device of claim 1, wherein the prosthetic device is configured to be deployed at the mitral valve.

15. The prosthetic device of claim 1, wherein the membrane comprises an upper portion and a lower portion, the upper portion of the membrane coupled to the upper portion of the expandable frame and disposed in the first heart chamber in the expanded deployed state, the lower portion of the membrane coupled to the first lower portion of the expandable frame and disposed in the second heart chamber in the expanded deployed state, the upper and lower portions of the membrane configured to curve around the first native leaflet without touching the first native leaflet or annulus.

* * * * *